United States Patent
Engler et al.

(10) Patent No.: US 9,868,870 B2
(45) Date of Patent: Jan. 16, 2018

(54) HYDROGEL COMPOSITIONS FOR DIRECT-WRITE PRINTING APPLICATIONS

(71) Applicant: International Business Machines Corporation, Armonk, NY (US)

(72) Inventors: Amanda C. Engler, Woodbury, MN (US); Wei Han, San Jose, CA (US); Hareem T. Maune, San Jose, CA (US); Alshakim Nelson, Montlake, WA (US); Ankit Vora, San Jose, CA (US); Rudy J. Wojtecki, San Jose, CA (US); Mu San Zhang, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 115 days.

(21) Appl. No.: 15/071,787

(22) Filed: Mar. 16, 2016

(65) Prior Publication Data
US 2017/0267883 A1    Sep. 21, 2017

(51) Int. Cl.
| | |
|---|---|
| *C09D 11/102* | (2014.01) |
| *C08L 71/02* | (2006.01) |
| *C09D 11/101* | (2014.01) |
| *A61L 27/18* | (2006.01) |
| *B05B 17/06* | (2006.01) |

(52) U.S. Cl.
CPC ............ *C09D 11/102* (2013.01); *A61L 27/18* (2013.01); *B05B 17/0607* (2013.01); *C09D 11/101* (2013.01); *A61L 2420/02* (2013.01)

(58) Field of Classification Search
CPC ....... C09D 11/10; C09D 11/16; C09D 11/102; C09D 11/101; A61L 27/16; A61L 27/26; A61L 27/52; A61L 27/56; B29L 317/0607
See application file for complete search history.

(56) References Cited

U.S. PATENT DOCUMENTS

| | | |
|---|---|---|
| 6,201,065 B1 | 3/2001 | Pathak et al. |
| 7,989,581 B2 | 8/2011 | Okawa |
| 8,044,111 B2 | 10/2011 | Chang et al. |
| 8,343,710 B1 | 1/2013 | Anseth et al. |

(Continued)

OTHER PUBLICATIONS

Barry, et al., "Direct-Write Assembly of 3D Hydrogel Scaffolds for Guided Cell Growth", Adv. Mater. 2009, 27, 2407-2410.

(Continued)

*Primary Examiner* — Sanza Mccledon
(74) *Attorney, Agent, or Firm* — Michael R. Roberts

(57) ABSTRACT

A thermo-responsive shear-thinning photo-curable composition comprises water, a linear amphiphilic polyether ABA triblock copolymer comprising at least one pendent ene group (*—CH=CH$_2$) capable of undergoing a thiol-ene reaction, a water-soluble crosslinking agent comprising two or more methylenethiol groups (*—CH$_2$SH), and a photoinitiator. Under non-shear conditions and a triblock copolymer concentration suitable for direct-write printing, the composition is a viscoelastic solid (hydrogel) at a temperature of about 15° C. to about 45° C., and is a free-flowing liquid (sol) between 0° C. and about 10° C. The hydrogel form can be shear-thinned at about 15° C. to about 45° C. to form a sol suitable for a direct-write printer using an extruding print-head. The compositions covalently crosslink when flood-exposed to ultraviolet radiation. The compositions have utility in forming three-dimensional scaffolds for growing living cells.

20 Claims, 29 Drawing Sheets

(56) References Cited

U.S. PATENT DOCUMENTS

| | | |
|---|---|---|
| 8,440,736 B2 | 5/2013 | Hoyle et al. |
| 8,784,893 B2 | 7/2014 | Daniloff et al. |
| 2004/0062793 A1 | 4/2004 | Dyke |
| 2005/0090612 A1 | 4/2005 | Soane et al. |
| 2005/0169491 A1 | 8/2005 | Pitt et al. |
| 2009/0208577 A1 | 8/2009 | Xu et al. |
| 2013/0026683 A1 | 1/2013 | Ng et al. |
| 2015/0011661 A1 | 1/2015 | Saxena et al. |
| 2015/0203627 A1 | 7/2015 | Sisson et al. |

OTHER PUBLICATIONS

Chang, et al., Direct-write Bioprinting Three-Dimensional Biohybrid Systems for Future Regenerative Therapies, J Biomed Mater Res B Appl Biomater. Jul. 2011; 98(1): 160-170.

Ciba, "Photoinitiators for UV Curing", brochure, copyright 2003, Ciba Specialty Chemicals.

Cohn, et al., "Improved reverse thermo-responsive polymeric systems", Biomaterials 24 (2003) 3707-3714.

Cohn, et al., "PEO—PPO—PEO-based poly(ether ester urethane)s as degradable reverse thermo-responsive multiblock copolymers", Biomaterials 27 (2006) 1718-1727.

Dimitrov, et al., "Synthesis and Associating Properties of Poly(ethoxyethyl glycidyl ether)/Poly(propylene oxide) Triblock Copolymers", Macromolecules 2004, 37, 1000-1008.

Hunt, et al., "Tunable, High Modulus Hydrogels Driven by Ionic Coacervation", Adv. Mater. 2011, 23, 2327-2331.

Jiang, Jun, "Rheology and Structure of Thermoreversible Hydrogels", Dissertation, Stony Brook University, Aug. 2007, copyright Jun Jiang.

Klouda, et al., "Thermoresponsive hydrogels in biomedical applications", European Journal of Pharmaceutics and Biopharmaceutics 68 (2008) 34-45.

Labbe, et al, "Controlled Polymerization of Glycidyl Methyl Ether Initiated by Onium Salt/Trilsobutylaluminum and Investigation of the Polymer LCST", Macromolecular Symposia, Special Issue: Advanced Polymer for Emerging Technologies, vol. 249-250, Issue 1, pp. 392-397, Apr. 2007, Abstract.

Lee, et al., "Poly(allyl Glycidyl Ether)—A Versatile and Functional Polyether Platform", Journal of Polymer Science Part A: Polymer Chemistry 2011, 49, 4498-4504.

Lewis, "Direct Ink Writing of 3D Functional Materials", Adv. Funct. Mater. 2006, 16, 2193-2204.

Naskar, et al., "Solution Behavior of Normal and Reverse Triblock Copolymers (Pluronic L44 and 10R5) Individually and in Binary Mixture", Langmuir 2012, 28, 7134-7146.

Ogura, et al., "Preparation and Solution Behavior of a Thermoresponsive Diblock Copolymer of Poly(ethyl glycidyl ether) and Poly(ethylene oxide)", Langmuir 2007, 23, 9429-9434.

Rouillard, et al., "Methods for Photocrosslinking Alginate Hydrogel Scaffolds with High Cell Viability", Tissue Engineering: Part C vol. 17, No. 2, 2011.

Sosnik, et al., "Reverse thermo-responsive poly(ethylene oxide) and poly(propylene oxide) multiblock copolymers", Biomaterials 26 (2005) 349-357.

Zhang, et al., "Dual-Responsive Hydrogels for Direct-Write 3D Printing", Macromolecules, 2015, 48 (18), pp. 6482-6488, submitted Jul. 13, 2015, published Aug. 31, 2015.

Coat

Cure

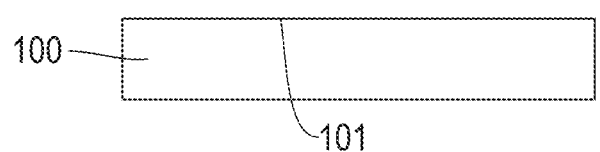
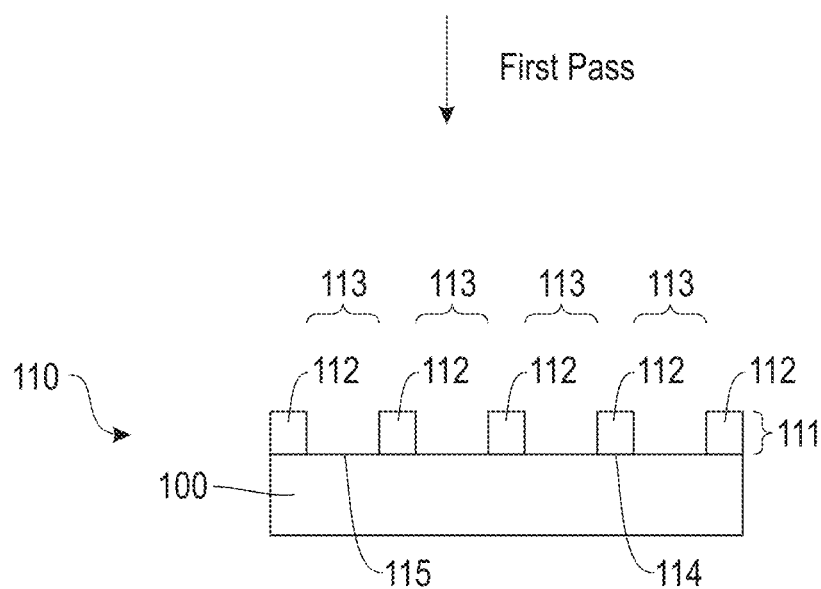

Second Pass

HYDROGEL COMPOSITIONS FOR DIRECT-WRITE PRINTING APPLICATIONS

STATEMENT REGARDING PRIOR DISCLOSURES BY THE INVENTOR OR A JOINT INVENTOR

The following disclosure(s) are submitted under 35 U.S.C. 102(b)(1)(A): M. ZHANG, et al., "Dual-Responsive Hydrogels for Direct-Write 3D Printing", Macromolecules, 2015, 48 (18), pp 6482-6488, submitted Jul. 13, 2015, published Aug. 31, 2015.

BACKGROUND

The present invention relates to hydrogel compositions for direct-write printing applications, and more specifically, to shear-thinning, thermo-responsive compositions for 3-dimensional (3D) printing that are capable of crosslinking in a liquid and/or hydrogel state.

Patterned hydrogels are of interest for a broad set of applications including drug delivery and tissue engineering. One emerging technology for patterning hydrogels is 3D printing, a form of additive manufacturing in which a 3-dimensional object is constructed one layer at a time. The engineering of 3D printers has matured since the 1980s when 3D printing was first developed for industrial-scale rapid prototyping. Temperature- and pH-responsive hydrogels have been demonstrated to have application in drug delivery and biomedicine. One of these is PLURONIC F127, a poly(ethylene oxide)-b-poly(propylene oxide)-b-poly(ethylene oxide) (PEO-PPO-PEO) triblock copolymer, attractive because of its thermo-reversible gel-forming properties in aqueous solution. A drawback of the F127 gel is its low yield strength. A high yield strength is desirable for tissue engineering and implantation applications. Another drawback of the F127 gel is its inability to form covalent crosslinks as an aqueous liquid and as a hydrogel. The F127 gel is believed to comprise entangled micelles of self-assembled PEO-PPO-PEO triblock copolymer, which are bound by non-covalent interactions. The micelles easily move past each other under shear, thus the low yield strength.

As 3D printing becomes more central to emerging biomedical technologies, a need grows for aqueous 3D printable inks that are crosslinkable as hydrogels while possessing thermal, rheological, and mechanical properties suitable for 3D printers. Preferably, these inks are "drop-in" materials conforming to the current requirements for 3D printer inks.

SUMMARY

Accordingly, a crosslinkable composition is disclosed, which comprises:

water;

an ABA type polyether triblock copolymer comprising a central hydrophilic poly(ethylene oxide) block (block B) linked to two peripheral hydrophobic polyether blocks (blocks A), wherein each of the blocks A comprises a random copolymer of i) a first repeat unit of formula (2):

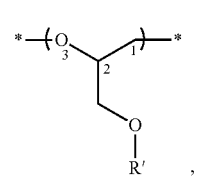

(2)

wherein R' is a monovalent $C_1$-$C_{10}$ hydrocarbon group selected from the group consisting of saturated alkyl groups and aromatic groups, and ii) a second repeat unit of formula (3):

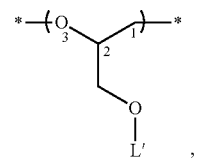

(3)

wherein L' is a monovalent $C_1$-$C_{10}$ hydrocarbon radical comprising an ene group (*—CH=$CH_2$) capable of undergoing a thiol-ene reaction;

a water-soluble crosslinking agent comprising two or more methylenethiol groups (*—$CH_2SH$); and a photoinitiator capable of abstracting hydrogen from a thiol group when exposed to ultraviolet light of wavelength 10 nm to 400 nm;

wherein the triblock copolymer, the crosslinking agent, and the photoinitiator are in contact with the solvent, the composition is a liquid at a temperature between 0° C. and about 10° C. and a shear-thinning viscoelastic solid at a temperature of about 15° C. to about 45° C. before crosslinking.

Further disclosed is a film layer comprising the above-described composition.

Also disclosed is method of printing, comprising:

providing a direct-write printer comprising a printer reservoir containing the composition of claim 1 at a temperature of about 15° C. to about 45° C., the printer equipped with an extruding print-head capable of disposing microdrops and/or strands of the composition pattern-wise onto a surface of a substrate;

extruding the microdrops and/or the strands of the composition from the print-head onto the surface using one or more passes of the print-head over the surface, thereby forming an initial structure comprising a stack of one more patterned layers of the composition disposed on the surface, the layers comprising a self-supporting non-covalently crosslinked hydrogel form of the composition; and flood-exposing the initial structure with ultraviolet light, thereby forming a photo-cured structure comprising a stack of one more photo-cured patterned layers, the photo-cured patterned layers comprising covalently crosslinked triblock copolymer.

Also disclosed is a photo-cured structure formed by the above-described method.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIGS. 2A-2G are cross-sectional and overhead layer diagrams illustrating a method of forming a three-dimensional layered structure by direct-write printing the composition using an extruding print-head at ambient temperature.

FIG. 7A shows the unstretched film. FIG. 7B shows the stretched film.

DETAILED DESCRIPTION

Figure 1A:
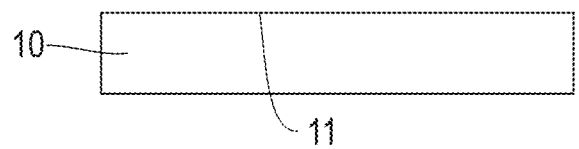
FIGS. 1A-1C are cross-sectional layer diagrams illustrating formation of a crosslinked film of the disclosed composition generated by conventional coating techniques.

Disclosed are aqueous photo-crosslinkable compositions useful as "inks" for direct-write printers utilizing an extrusion print-head. Direct-write printing refers to an additive deposition process for constructing three-dimensional multi-layered structures disposed on a substrate without using lithography. The features of the structures are defined by computer-aided design/computer-aided manufacturing (CAD/CAM) software. Direct-write printing is also referred to herein as "three-dimensional printing" or simply "3D printing". The compositions comprise water, a multi-functional thiol crosslinking agent, a shear-thinning thermoresponsive polyether triblock copolymer (TBC) capable of undergoing a crosslinking thiol-ene reaction with the crosslinking agent, a photoinitiator for activating the thiol-ene reaction, and any optional additives. The triblock copolymer, the crosslinking agent, and the photoinitiator are in contact with the solvent in the form of dispersed and/or dissolved materials. The mechanical and thermal properties of the compositions provide improved dimensional stability of initial structures prior to crosslinking the composition. The direct-write printer reservoir can contain the composition in the form of a liquid (sol) or a viscoelastic solid (i.e., a self-supporting hydrogel, or simply "gel").

The composition is capable of photo-crosslinking at a temperature between 0° C. and about 45° C. (i.e., as a liquid and/or as a gel).

When used in a direct-write printer operating at a temperature of about 15° C. to about 45° C., the shear-thinning composition can be extruded as a liquid to form a self-supporting initial structure as a non-crosslinked hydrogel. Flood-exposing the initial structure to a suitable wavelength of ultraviolet light initiates the thiol-ene reaction, thereby producing a crosslinked structure. The crosslinked structure can have utility in tissue engineering, implants, diagnostic platforms, drug delivery systems, and environmental or bio sensors.

The non-crosslinked compositions have two useful properties for direct-write printing. First, the compositions can be reversibly temperature cycled from a low viscosity free-flowing liquid (sol) to a high viscosity gel. For example, at a concentration suitable for direct-write printing (e.g., about 10-30 wt % in TBC) the composition can be a free-flowing liquid (sol) at a temperature between 0° C. and about 10° C., which reversibly heat-thickens to become a self-supporting gel (i.e., viscoelastic solid) when heated to about 15° C. to about 45° C. under non-shear conditions. Cooling the gel to between 0° C. and about 10° C. restores the liquid form. This thermo-responsive property allows the compositions to be conveniently loaded into a printer reservoir as a cold liquid.

Second, the non-crosslinked compositions are shear-thinning. Applying a constant shear stress to the self-supporting gel at about 15° C. to about 45° C. (e.g., as in a working extrusion print-head operating at ambient temperature), the hydrophobic interactions supporting the non-crosslinked gel network rapidly break down generating a free-flowing liquid that remains a liquid as long as the shear stress is applied. Removing the shear stress from the liquid at temperatures of about 15° C. to about 45° C. (e.g., after the composition has passed through the print nozzle) causes a rapid increase in viscosity in the non-crosslinked liquid composition, restoring the gelled state. Thus, the composition exits the nozzle of the print-head as a liquid and becomes a self-supporting gel soon thereafter, reaching a maximum viscosity when disposed on a substrate surface under non-shear conditions. The extruded composition exiting the nozzle can have the form of a microdrop and/or a strand, whose shape and dimensions can be substantially or wholly preserved in the non-crosslinked composition disposed on the substrate. The microdrop and/or strand can have any suitable shape and dimensions within the capability of the direct-write printer. The microdrops and/or strands can be deposited in one or more passes of the print nozzle over one or more regions of a surface of a substrate to construct a self-supporting non-crosslinked initial structure.

The non-crosslinked initial structure has improved dimensional stability compared to an otherwise identical non-crosslinked structure prepared using an aqueous solution of poly(ethylene oxide)-b-poly(propylene oxide)-b-poly(ethylene oxide) (PEO-PPO-PEO) triblock copolymer as the direct-write printer "ink". For example, a multi-layered micro-pillar comprising the non-crosslinked composition can sag less and have improved sidewall verticality compared to an identically sized micro-pillar printed using aqueous PEO-PPO-PEO of the same concentration.

The initial structure can comprise one or more printed layers and have any suitable shape and dimensions within the capabilities of the CAD/CAM software and the direct-write printer. The initial structure can be covalently crosslinked by flood-exposing the structure to a suitable wavelength (10 nm to 400 nm) of ultraviolet light for a suitable period of time (about 1 sec to about 24 hours).

In an embodiment, the crosslinked printed structure is a scaffold for depositing and growing cellular tissue. A scaffold for cellular growth can have any suitable three-dimensional shape or dimensions. As a non-limiting example, a scaffold can comprise a stack of alternating layers of parallel spaced strands comprising the composition, wherein the strands of adjacent layers are oriented orthogonal to one another. The crisscrossed strands of adjacent layers do not make contact except at overlap regions of the strands.

Thiol-ene Reaction

Scheme 1 illustrates an example of a thiol-ene reaction (i.e., thiol addition to an olefin to form a sulfide) mediated by a photoinitiator.

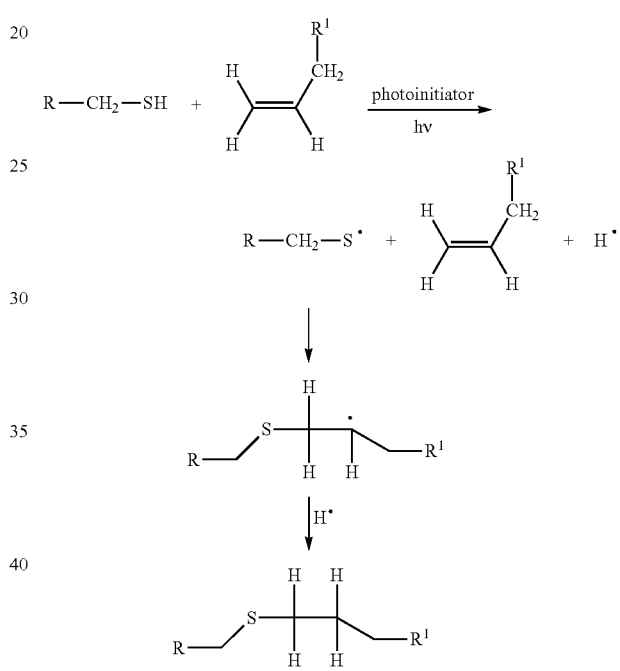

In the above example, the thiol compound comprises a methylenethiol group (*—$CH_2SH$). The olefin material comprises an allyl group ($CH_2$=CH—$CH_2$—*). When exposed to a suitable wavelength of ultraviolet light, the photoinitiator abstracts hydrogen from the thiol forming a thiol radical. The thiol radical adds to the double bond to form a carbon radical, which combines with the hydrogen radical forming a carbon-hydrogen single bond. The final product is a sulfide (i.e., thioether). The R and $R^1$ groups can be any suitable group that does not adversely affect the thiol-ene reaction and/or the gel modulus.

The crosslinking agent of the composition comprises two or more methylenethiol groups.

The TBC comprises at least one ene group capable of undergoing a thiol-ene reaction with the crosslinking agent. The ene group can also be used to introduce other chemical functionality to the TBC (e.g., by a thiol-ene reaction, Michael addition reaction to the olefin, oxidation of the double bond, and/or another reaction).

Triblock Copolymer

The TBC is an amphiphilic polyether triblock copolymer capable of forming a non-covalently crosslinked, thermoresponsive, shear-thinning self-supporting gel in water. For example, at a temperature between 0° C. and about 8° C. and no applied shear stress, a 15 wt % aqueous solution of the TBC can be a free-flowing liquid having a storage modulus G' and loss modulus G" less than 100 Pa. When heated to a temperature of about 10° C. to about 45° C., the cold liquid can undergo a reversible sol-gel transition forming a shear thinning non-crosslinked self-supporting gel having G' greater than 10000 Pa and G" greater than 1000 Pa. Without being bound by theory, the gel is believed to be a network of entangled self-assembled micellar particles of the triblock copolymer, which are bound by non-covalent hydrophobic interactions. Heating the cold liquid solution likely promotes increased hydrophobic interactions by disrupting water structure around the triblock copolymer chains, forming shear thinning hydrogel network. The water structure reforms upon cooling the gel, resulting in a low viscosity liquid. The liquid and gel forms can be clear and colorless, indicating that the triblock copolymer does not form macroscopic precipitates at elevated temperature.

The triblock copolymers are ABA type block copolymers comprising a central hydrophilic poly(ethylene oxide) B block, which is linked to two peripheral hydrophobic poly (substituted ethylene oxide) A blocks.

More specifically, the B block has a structure according to formula (1):

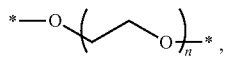

(1)

wherein n represents average degree of polymerization and n has a value of about 20 to about 450. The B block is covalently linked via terminal oxygens to respective end groups of the A blocks.

Herein, an atomic center shown covalently linked to an asterisk means the atomic center is covalently linked to another unspecified portion of the chemical structure (e.g., another of the same repeat unit, a different repeat unit, polymer chain end group). It should be understood the bond with an asterisk (starred bond) is not a methyl group.

Each of the A blocks is a random copolymer chain comprising a first substituted ethylene oxide repeat unit (first repeat unit) of formula (2):

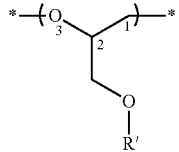

(2)

wherein atomic centers of the polymer backbone are numbered and R' is a monovalent $C_1$-$C_{10}$ hydrocarbon group selected from the group consisting of saturated alkyl groups and aromatic groups.

Non-limiting saturated alkyl groups include methyl, ethyl, n-propyl, iso-propyl, n-butyl, sec-butyl, t-butyl, cyclopentyl, n-pentyl, iso-pentyl, n-hexyl, cyclohexyl, n-octyl, 2-ethylhexyl, n-nonyl, and n-dodecyl Non-limiting aromatic groups include phenyl, 2-methylphenyl, 4-methylphenyl, and benzyl.

In an embodiment, R' is selected from the group consisting of methyl, ethyl, n-propyl, iso-propyl, n-butyl, sec-butyl, and t-butyl. In another embodiment, R' is iso-propyl.

First repeat units of formula (2) can be present singularly or in combination.

Each of the A blocks also comprises a second substituted ethylene oxide repeat unit (second repeat unit) of formula (3):

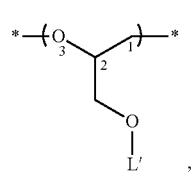

(3)

wherein atomic centers of the polymer backbone are numbered, and L' is a monovalent $C_1$-$C_{10}$ hydrocarbon radical comprising an ene group:

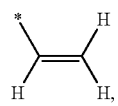

also written as *—CH=CH$_2$. The ene group is capable of undergoing a thiol-ene reaction.

Preferably, L' comprises an allyl group:

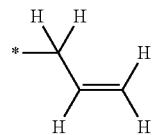

also written as *—CH$_2$CH=CH$_2$. The allyl group is capable of undergoing a thiol-ene reaction. In an embodiment, the second repeat unit has a structure (I):

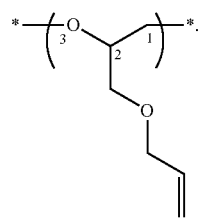

(I)

The first and second repeat units of the A blocks are linked in a head-to-tail manner. The oxygen labeled 3 is designated the head, and the methylene carbon labeled 1 is designated the tail.

The first and/or second repeat units can be stereospecific or non-stereospecific.

Each A block comprises 10 to 100, more particularly 10 to 50, and even more particularly 10 to 30 of the first repeat units. Each A block also comprises at least one second repeat unit, more preferably 1 to 10 second repeat units, and even more preferably 1 to 5 second repeat units. The molar ratio of first to second repeat units can be about 100:1 to about 3:1, more particularly 20:1 to 5:1. In an embodiment, the molar ratio of first to second repeat units is about 10:1 to 8:1.

The triblock copolymer is a linear polymer chain, meaning the polymer backbone has one polymer branch (as in a segment of rope) rather than intersecting polymer branches, and the polymer chain has two dangling ends. Each end group is an independent monovalent radical selected from the group consisting of hydrogen, and acyl groups comprising 1-10 carbons (e.g., acetyl, propionyl, benzoyl, and the like). In an embodiment, each end group is hydrogen.

More specific triblock copolymers have a structure according to formula (4):

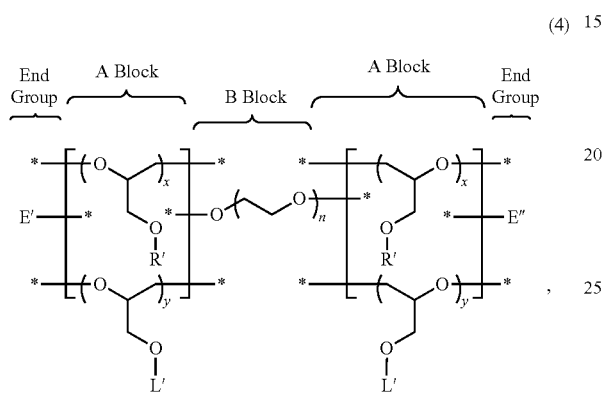

(4)

wherein
subscripts x, y, and n represent average degree of polymerization of the corresponding repeat unit contained in parentheses, and x, y, and n independently have values greater than 0,
E' is a first end group,
E" is a second end group,
each L' is a monovalent radical comprising an ene group (*—CH=CH$_2$) capable of undergoing a thiol-ene reaction, and
each R' is a monovalent C$_1$-C$_{10}$ hydrocarbon radical selected from the group consisting of saturated alkyl groups, and aromatic groups.

In the above structure, each linear A block polymer chain is enclosed by square brackets. Vertical stacking of the repeat units (enclosed by parentheses) within the square brackets indicates a random distribution of the repeat units within each A block. The B block comprises a poly(ethylene oxide) chain, also referred to herein as a PEG block after poly(ethylene glycol) (PEG). End group E' is linked to a terminal oxygen of either a first repeat unit or a second repeat unit of a first A block. End group E" is linked to a terminal oxygen of a first repeat unit or a second repeat unit of a second A block. A first terminal oxygen of the B block is linked to terminal carbon of a first repeat unit or a second repeat unit of a first A blocks. A second terminal oxygen of the B block is linked to a terminal carbon of a first repeat unit or a second repeat unit of a second A block.

Subscripts n, x and y can be in a ratio n:(x+y) of about 9:1 to about 30:1.

In a preferred embodiment, R' is isopropyl and L' is allyl. In another preferred embodiment, x is about 19, y is about 2, and n is about 181. In another preferred embodiment, each of E' and E" is hydrogen.

Preparation of the Triblock Copolymer

The triblock copolymers are preferably prepared by a ring opening polymerization (ROP) of a mixture of glycidyl ether monomers. The reaction mixture comprises a solvent, a first glycidyl ether monomer comprising the above-described R' moiety, a second glycidyl ether monomer comprising an ene group capable of undergoing a thiol-ene reaction, a poly (ethylene glycol) (PEG) initiator, an organocatalyst, and optionally an accelerator for the ROP.

The first and/or second glycidyl ether monomers can be used singularly or in combination. The first and/or second glycidyl ether monomers can be stereospecific or non-stereospecific.

The first glycidyl ether monomer has a structure according to formula (5):

(5)

wherein R' is a monovalent C$_1$-C$_{10}$ hydrocarbon radical selected from the group consisting of saturated alkyl groups and aromatic groups.

Non-limiting saturated alkyl groups include methyl, ethyl, n-propyl, iso-propyl, n-butyl, sec-butyl, t-butyl, cyclopentyl, n-pentyl, iso-pentyl, n-hexyl, cyclohexyl, n-octyl, 2-ethylhexyl, n-nonyl, and n-dodecyl.

Non-limiting aromatic groups include phenyl, 2-methylphenyl, 4-methylphenyl, and benzyl.

In an embodiment, R' is selected from the group consisting of methyl, ethyl, n-propyl, iso-propyl, n-butyl, sec-butyl, and t-butyl. In another embodiment, R' is iso-propyl.

First glycidyl ether monomers can be present singularly or in combination.

Thus, non-limiting first glycidyl ether monomers include methyl glycidyl ether, ethyl glycidyl ether, n-propyl glycidyl ether, iso-propyl glycidyl ether, n-butyl glycidyl ether, sec-butyl glycidyl ether, t-butyl glycidyl ether, cyclopentyl glycidyl ether, n-pentyl glycidyl ether, iso-pentyl glycidyl ether, n-hexyl glycidyl ether, cyclohexyl glycidyl ether, n-octyl glycidyl ether, 2-ethylhexyl glycidyl ether, n-nonyl glycidyl ether, n-dodecyl glycidyl ether, phenyl glycidyl ether, 2-methylphenyl glycidyl ether, 4-methylphenyl glycidyl ether, and benzyl glycidyl ether.

In an embodiment, the first glycidyl ether monomer is selected from the group consisting of methyl glycidyl ether, ethyl glycidyl ether, n-propyl glycidyl ether, iso-propyl glycidyl ether, n-butyl glycidyl ether, sec-butyl glycidyl ether, and t-butyl glycidyl ether.

In a preferred embodiment, the first glycidyl ether monomer is iso-propyl glycidyl ether.

The second glycidyl ether monomer has a structure according to formula (6):

(6)

wherein L' is a monovalent radical comprising an ene group (*—CH=CH$_2$) capable of undergoing a thiol-ene reaction.

In an embodiment, L' is allyl and the second glycidyl ether monomer is allyl glycidyl ether (AGE):

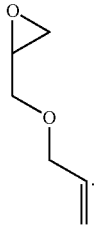

The poly(ethylene glycol) (PEG) initiator for the ROP has the structure:

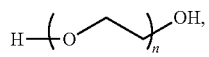

wherein n represents average degree of polymerization, and n has a value of about 20 to about 450, more preferably 100 to 300.

The PEG initiator can have a number average molecular weight (Mn) of about 1000 to about 20000, more preferably 4000 to 14000.

The amount of PEG initiator is calculated based on the equivalent molecular weight per nucleophilic initiator group in the dinucleophilic initiator. The initiator groups are preferably present in an amount of 0.001 to 10.0 mol %, 0.1 to 2.5 mol %, 0.1 to 1.0 mol %, and 0.2 to 0.5 mol %, based on total moles of glycidyl ether monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

The polymerization catalyst is preferably an organocatalyst whose chemical formula comprises no alkali metal, alkaline earth metal, and no metal of Groups 3 to 12 of the Periodic Table.

Base organocatalysts for ROPs include tertiary amines such as triallylamine, triethylamine, tri-n-octylamine, benzyldimethylamine, and 4-dimethylaminopyridine, phosphines, N-heterocyclic carbenes (NHC), bifunctional aminothioureas, phosphazenes, amidines, and guanidines.

Other base organocatalysts include phosphazene bases such as, for example, tert-butylimino-tri(pyrrolidino)phosphorane (P$_1$-t-Bu), 1-ethyl-2,2,4,4,4-pentakis(dimethylamino)-2λ5,4λ5-catenadi(phosphazene) (P$_2$-Et), 1-tert-butyl-2,2,4,4,4-pentakis(dimethylamino)-2λ5,4λ5-catenadi(phosphazene) (P$_2$-t-Bu), 1-tert-octyl-4,4,4-tris(dimethylamino)-2,2-bis[tris(dimethylamino)phosphoranylidenamino]-2λ5,4λ5-catenadi(phosphazene) (P$_4$-t-Oct), and 1-tert-butyl-4,4,4-tris(dimethylamino)-2,2-bis[tris(dimethylamino)-phosphoranylidenamino]-2λ5,4λ5-catenadi(phosphazene) (P$_4$-t-Bu) sold by Sigma Aldrich.

A particularly preferred phosphazene is P$_4$-t-Bu:

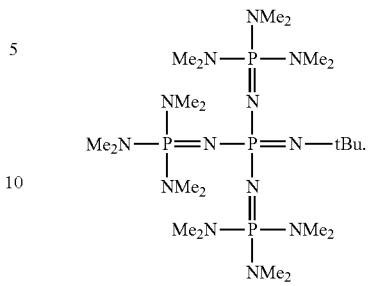

A thiourea ROP organocatalyst is N-(3,5-trifluoromethyl)phenyl-N'-cyclohexyl-thiourea (TU):

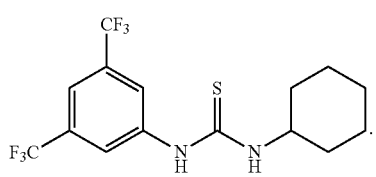

Other ROP organocatalysts comprise at least one 1,1,1,3,3,3-hexafluoropropan-2-ol-2-yl (HFA) group. Singly-donating hydrogen bond catalysts have the formula (C-1):

$$R^2—C(CF_3)_2OH \quad (C-1),$$

wherein R$^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Scheme 2.

Scheme 2.

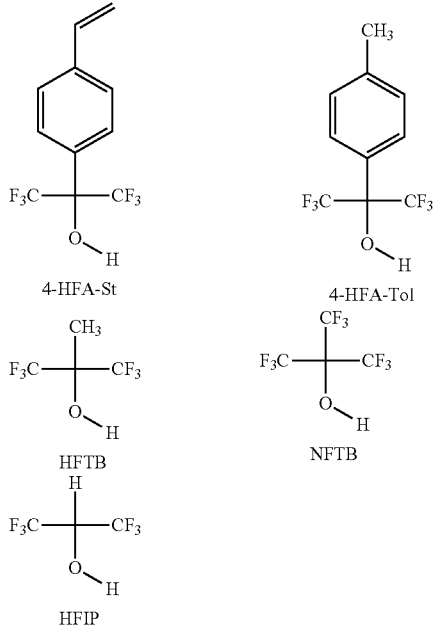

Doubly-donating hydrogen bonding catalysts have two HFA groups, represented by the general formula (C-2):

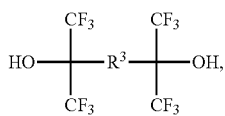
(C-2)

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (C-2) include those listed in Scheme 3. In a specific embodiment, $R^2$ is an arylene or substituted arylene group, and the HFA groups occupy positions meta to each other on the aromatic ring.

Scheme 3.

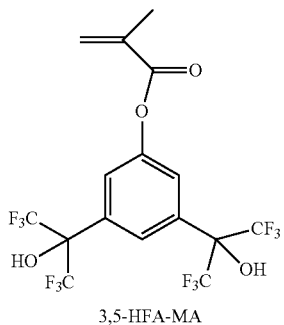

3,5-HFA-MA

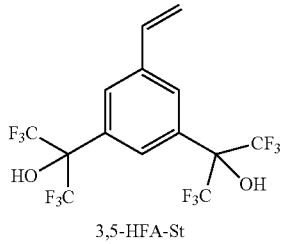

3,5-HFA-St

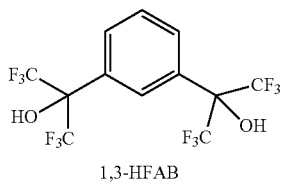

1,3-HFAB

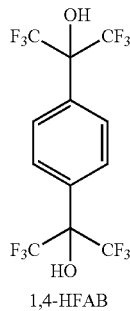

1,4-HFAB

Preferred hydrogen bonding catalysts include 4-HFA-St, 4-HFA-Tol, HFTB, NFTB, HPIP, 3,5-HFA-MA, 3,5-HFA-St, 1,3-HFAB, 1,4-HFAB, and combinations thereof.

The HFA catalyst can be bound to a support. In one embodiment, the support comprises a polymer, a crosslinked polymer bead, an inorganic particle, or a metallic particle. HFA-containing polymers can be formed by known methods including direct polymerization of an HFA-containing monomer (for example, the methacrylate monomer 3,5-HFA-MA or the styryl monomer 3,5-HFA-St). Functional groups in HFA-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl groups, $C_1$-$C_{12}$ heteroalkyl groups, ether groups, thioether groups, amino groups, ester groups, amide groups, and combinations thereof. Also contemplated are catalysts comprising charged HFA-containing groups bound by ionic association to oppositely charged sites on a polymer or a support surface.

The ROP catalyst can be an acid organocatalyst (e.g., diphenylphosphate (DPP), triflic acid, and the like).

The ROP reaction mixture comprises at least one ROP catalyst and, when appropriate, several ROP catalysts together. The ROP catalyst is added in a proportion of 1/20 to 1/40,000 moles relative to the glycidyl ether monomers, and preferably in a proportion of 1/1,000 to 1/20,000 moles relative to the glycidyl ether monomers.

The ROP polymerization can be conducted in the presence of an optional accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Scheme 4.

Scheme 4.

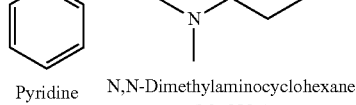

Pyridine (Py)   N,N-Dimethylaminocyclohexane ($Me_2NCy$)

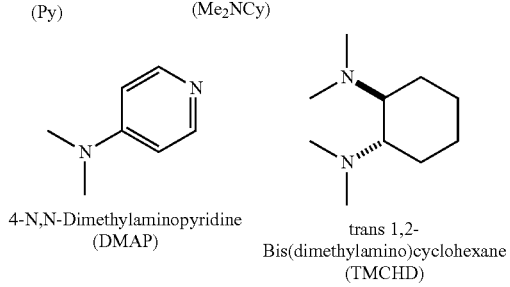

4-N,N-Dimethylaminopyridine (DMAP)   trans 1,2-Bis(dimethylamino)cyclohexane (TMCHD)

-continued

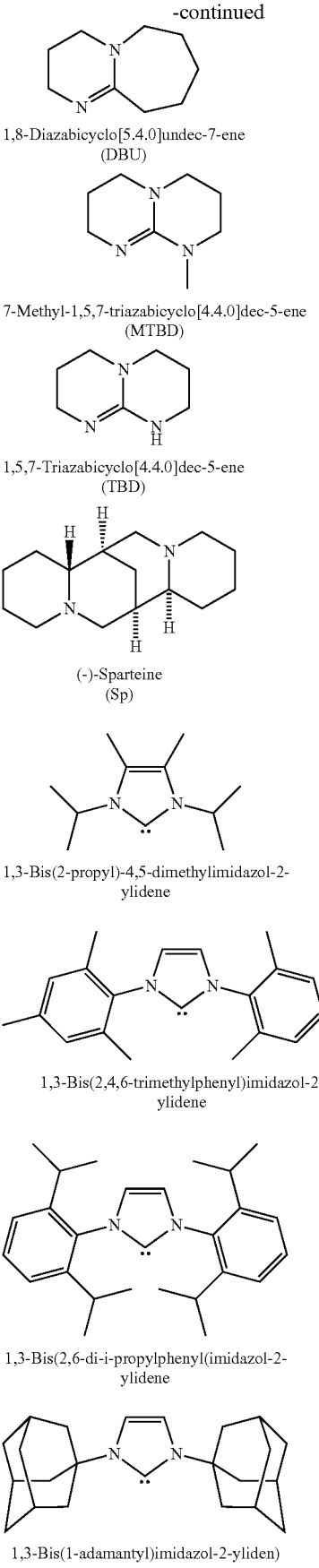

1,8-Diazabicyclo[5.4.0]undec-7-ene
(DBU)

7-Methyl-1,5,7-triazabicyclo[4.4.0]dec-5-ene
(MTBD)

1,5,7-Triazabicyclo[4.4.0]dec-5-ene
(TBD)

(−)-Sparteine
(Sp)

1,3-Bis(2-propyl)-4,5-dimethylimidazol-2-ylidene (Im-1)

1,3-Bis(2,4,6-trimethylphenyl)imidazol-2-ylidene (Im-2)

1,3-Bis(2,6-di-i-propylphenyl(imidazol-2-ylidene (Im-3)

1,3-Bis(1-adamantyl)imidazol-2-yliden) (Im-4)

-continued

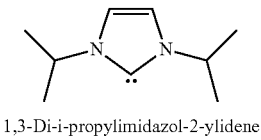

1,3-Di-i-propylimidazol-2-ylidene (Im-5)

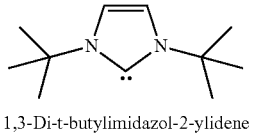

1,3-Di-t-butylimidazol-2-ylidene (Im-6)

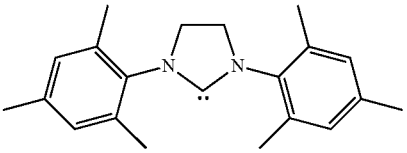

1,3-Bis(2,4,6-trimethylphenyl)-4,5-dihydroimidazol-2-ylidene (Im-7)

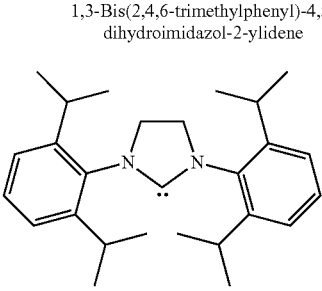

1,3-Bis(2,6-di-i-propylphenyl)-4,5-dihydroimidazol-2-ylidene (Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on the equivalent molecular weight per nucleophilic initiator group of the initiator.

The catalyst is preferably used in an amount of 0.005 to 2.0 weight % (wt %), more preferably 0.03 to 1.0 wt % based on total weight of glycidyl ether monomers of the reaction mixture.

Non-limiting solvents for the polymerization include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter.

The ROP polymerization can be performed at a temperature that is about ambient temperature or higher, 15° C. to 100° C., and more specifically ambient temperature. Reaction times vary with solvent, temperature, agitation rate, pressure, and equipment, but in general the polymerizations are complete within about 1 hour to about 48 hours.

The ROP polymerization is conducted using an inert (i.e., dry) atmosphere, such as nitrogen or argon, and at a pressure of from 100 to 500 MPa (1 to 5 atm), more typically at a pressure of 100 to 200 MPa (1 to 2 atm). At the completion of the reaction, the solvent can be removed using reduced pressure.

Endcap Agents

An endcap agent can prevent further chain growth after the ROP and stabilize the reactive end groups from unwanted side reactions, such as chain scission. Endcap agents include, for example, compounds for converting terminal hydroxyl groups to esters, such as acid anhydrides (e.g., acetic anhydride), acid chlorides (acetyl chloride), and/or active esters (e.g., p-nitrophenyl esters). Other endcap agents include alkyl and aryl isocyanates, which form carbamates (urethanes) with terminal hydroxy groups. Other endcap agents include alkylating agents capable of forming alkyl ethers, aromatic ethers including benzyl ethers, silyl ethers, acetals, ketals, and the like. Still other endcap agents include perhalogenated (e.g., perfluorinated) derivatives of any of the foregoing endcap agents. In an embodiment, the endcap agent is acetic anhydride, which converts reactive hydroxy end groups to acetate ester groups.

The triblock copolymer preferably has a number average molecular weight Mn as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the final block polymer has a number average molecular weight Mn of 8,000 to 40,000 g/mole.

The triblock copolymer can have a narrow polydispersity index (PDI), generally from 1.01 to 2.0, more particularly 1.01 to 1.30, and even more particularly 1.01 to 1.25.

The composition comprises the triblock copolymer in an amount of 10 wt % to 25 wt %, more preferably 12 wt % to 20 wt %, and most preferably about 15 wt % based on total weight of the composition.

Crosslinking Agents

The compositions for direct-write printing comprise a water-soluble crosslinking agent comprising two or more methylenethiol groups (*—CH$_2$SH). Non-limiting examples of water-soluble crosslinking agents include 1,2-ethanedithiol, 1,3-propanedithiol, and 1,4-dithiothreitol.

Other crosslinking agents include PEG dithiols of formula (7):

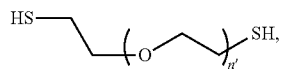

(7)

wherein n' represents average degree of polymerization, and n' has a value of 1 to 300.

The composition comprises the multi-functional thiol crosslinking agent in an amount wherein the molar ratio of methylenethiol groups to ene groups of the TBC is about 1:1.

Photoinitiators

The photoinitiator is capable of abstracting hydrogen from a thiol when exposed to ultraviolet light having a wavelength between 10 nm to 400 nm, more particularly between 150 nm to 400 nm, and even more particularly between 300 nm to 400 nm. In an embodiment, the thiol-ene reaction is initiated using a light source emitting ultraviolet light of wavelength 310 nm.

Non-limiting photoinitiators include benzophenones, acetophenone derivatives, such as alpha-hydroxyalkylphenylketones, benzoin alkyl ethers, benzil ketals, monoacylphosphine oxides, and bis-acylphosphine oxides. In an embodiment, the photoinitiator is an alpha-hydroxyalkylphenylketone.

Other photoinitiators include mercaptobenzothiazoles, mercaptobenzooxazoles and hexaryl bisimidazole.

More specific photoinitiators include ethyl 2,4,6-trimethylbenzoylphenyl phosphinate (Lucirin TPO-L), benzophenone (IRGACURE 500), 1-hydroxy-cyclohexyl-phenyl-ketone (IRGACURE 184), 2-hydroxy-2-methyl-1-phenyl-1-propanone (DAROCUR 1173), 2,2-dimethoxy-2-phenyl acetophenone (IRGACURE 651), 2-Hydroxy-1-[4-(2-hydroxyethoxy)phenyl]-2-methyl-1-propanone (IRGACURE 2959), Methyl benzoylformate (DAROCUR MBF), oxyphenyl-acetic acid 2-[2-oxo-2-phenyl-acetoxy-ethoxy]-ethyl ester and oxy-phenyl-acetic 2-[2-hydroxy-ethoxy]-ethyl ester (IRGACURE 754), alpha, alpha-dimethoxy-alpha-phenylacetophenone (IRGACURE 651), 2-benzyl-2-(dimethylamino)-1-[4-(4-morpholinyl) phenyl]-1-butanone (IRGACURE 369), 2-methyl-1-[4-(methylthio)phenyl]-2-(4-morpholinyl)-1-propanone (IRGACURE 907), and diphenyl (2,4,6-trimethylbenzoyl)-phosphine oxide (DAROCUR TPO).

The composition comprises the photoinitiator in an amount of between 0 wt % and 10 wt %, preferably between 2 wt % and 8 wt % based on total weight of the ene-containing monomer(s) of the polymer. The total weight of the ene-containing monomer of the triblock polymer was obtained by NMR analysis as follows. The number average molecular weight of the polymer (Mn) was determined by NMR. The number of ene-containing monomer units of the polymer was then determined by NMR and the total weight of the ene-containing monomer was calculated. For example, if four allyl glycidyl ether (MW 114.14 g/mol) units were found per ABA triblock chain whose blocks have Mn values of 2 k, 8 k, and 2 k, respectively, then 1 mole (2000+8000+2000=12000 g) of ABA triblock polymer contains 4 mol×114.14 g/mol=456.6 g ene-containing monomer, which amounts to 456.6/12000×100%=3.8 wt % of the total weight of the polymer. Thus, if 0.4 g of polymer is used and the amount of photoinitiator used is 5 wt % of the total ene-containing monomer present, then the amount of ene-containing monomer of the polymer is 0.038×0.4 g=0.0152 g and the amount of photoinitiator is 0.05×0.0152 g=0.76 mg.

Additives

Non-limiting exemplary additives for the ink compositions include diluent synthetic polymers (e.g., PEG, polypropylene glycol, poly(vinyl alcohol), poly(methacrylic acid)), drugs (e.g., antibiotics such as penicillin and streptomycin), cell nutrients (e.g., proteins, peptides, amino acids, vitamins, carbohydrates (e.g., starches, celluloses, glycogen), and minerals (e.g., calcium, magnesium, iron), synthetic or naturally occurring nucleic acids, surfactants, plasticizers, salts (e.g., sodium chloride, potassium chloride, phosphate salts, acetate salts), living cells, and cell components (e.g., elastin, fibrin, proteoglycans).

The composition can comprise one or more additives in an amount of 0 wt % to about 25 wt % of the composition, based on total weight of the composition.

Cells

Living cells include prokaryotic and eukaryotic cells. Non-limiting examples of eukaryotic cells include mammalian cells (e.g., stem cells, progenitor cells and differentiated cells). Stem cells have the ability to replicate through numerous population doublings (e.g., at least 60-80), in some cases essentially indefinitely, and also have the ability to differentiate into multiple cell types (e.g., pluripotent or multipotent). Other living cells include immortalized cells that due to mutation do not undergo normal replicative senescence, and can proliferate essentially indefinitely. Other living cells include embryonic stem cells, amniotic fluid stem cells, cartilage cells, bone cells, muscle cells, skin cells, pancreatic cells, kidney cells, nerve cells, and liver cells.

The composition can comprise a living cell in an encapsulated form. Encapsulated cells are cells or small clusters of cells or tissue that are surrounded by a selective membrane laminate that allows passage of oxygen and other required metabolites, releases certain cell secretions (e.g., insulin), but limits the transport of the larger agents of the host's immune system to prevent immune rejection. Encapsulation can be useful for implanting and/or injecting cells or tissues containing living xenogeneic or allogeneic cells while reducing the risk of immune rejection in a host. This can be useful in treating diseases due to inadequate or loss or secretory cell function, or ailments that would benefit from the addition of certain secretory cells such as acute liver failure, type I diabetes, chronic pain, Parkinson's disease, and other diseases. Other uses of encapsulated cells include, but are not limited to, single cell analysis, high throughput drug screening, and stem cell differentiation at the single cell level. The cells can be encapsulated in a microcapsule of from 50 or 100 micrometers to 1 or 2 mm in diameter. The microcapsules can include one or more living cells, preferably 1 to 10 living cells, more preferably 1 to 5 living cells.

Also disclosed is a method of forming a composition for 3D printing comprising combining at a temperature between 0° C. and about 6° C. i) water, ii) a disclosed triblock copolymer, iii) a water-soluble crosslinking agent comprising two or more methylene thiol groups, iv) a photoinitiator, and v) any optional additives, thereby forming the composition. The composition can comprise a living cell or an organism comprising a living cell.

Film Formation

Figure 1B:
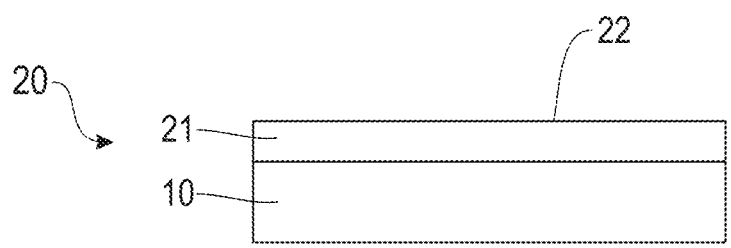
Figure 1C:
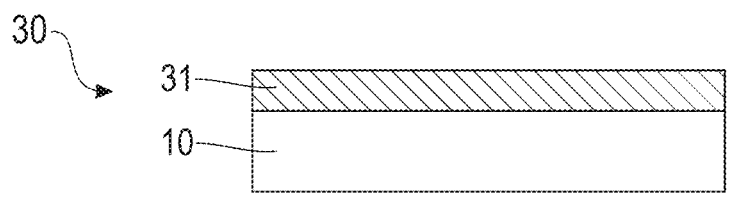

The composition has utility in forming film layers using conventional coating techniques (e.g., spin coating, dip coating, roll coating, spray coating, and the like), illustrated by the cross-sectional layer diagrams of FIGS. 1A-1C. The composition is preferably applied in the form of a liquid having a temperature below the sol-gel temperature of the composition, more particularly between 0° C. and about 8° C. The liquid is applied to surface 11 of a substrate 10 (FIG. 1A). Substrate 10 can be any suitable base material (e.g., flexible film base, glass plate, metal foil, and the like). Substrate 10 can comprise one layer (shown) or more layers (not shown). Surface 11 of substrate 10 preferably has a temperature above the sol-gel transition temperature of the composition, more particularly 15° C. to 45° C. Applying the composition onto surface 11 results in structure 20 comprising film layer 21 disposed on substrate 10. Preferably, film layer 21 comprises the composition in the form of a self-supporting viscoelastic solid (gel) containing non-crosslinked triblock copolymer. Film layer 21 can have any suitable thickness. Film layer 21 preferably comprises all or substantially all of the water of the composition as formulated. Film layer 21 can be separated from the underlying substrate as a free-standing film if desired. Optionally, the process of forming film layer 21 can be repeated one or more times, applying the liquid composition (or a different liquid composition) each time to a previously formed film layer, thereby forming a structure comprising a stack of two or more film layers disposed on substrate 10, wherein at least one of the film layers comprises the composition (not shown).

Film layer 21 can be cured by flood-exposing film layer 21 to a suitable wavelength of ultraviolet light for a suitable period of time. The flood-exposure can be performed before (shown) or after drying film layer 21 (not shown). The resulting structure 30 comprises cured film layer 31 (FIG. 1C). In this example, cured film layer 31 is a self-supporting viscoelastic solid comprising all or substantially all of the water of the composition as formulated. Cured film layer 31 also comprises crosslinked triblock copolymer generated by the thiol-ene reaction. Optionally, cured film layer 31 can be dried and/or separated from the substrate to form a free-standing film (not shown). The free-standing film can comprise one or more layers, wherein at least one of the layers comprises the cured (crosslinked) composition.

3D Printing

Also disclosed is a method of forming a 3D layered structure by direct-write printing the composition. An ink reservoir of a 3D printer is loaded with the composition. Preferably, the reservoir has a temperature below a sol-gel transition temperature of the composition, at which the composition is a liquid. The printer is equipped with a piezoelectric print-head capable of delivering microdrops of the composition pattern-wise onto a print surface. Herein, the print surface can be a top surface of a substrate or a top surface of a previously printed layer.

The construction of the 3D layered structures is computer controlled and is done in a laminar fashion. In one configuration, the dispensing head of the printer moves in the z direction and the fabrication platform supporting the printed object moves in the x and y directions. In another configuration, the dispensing head moves in 3 dimensions and the fabrication platform is stationary. In another configuration, the fabrication platform moves in 3 dimensions and the dispensing head is stationary. The dispensing head can dispense continuously to generate microstrands of the composition, or discontinuously to dispense microdrops of the composition. Liquid flow can be controlled by air pressure (pneumatic nozzle) or using a stepper motor (volume-driven injection). The strand thickness can be modulated by varying the deposition speed, tip diameter, and/or the applied pressure. Strand thickness or the line width is also a function of viscosity of the hydrogel and interaction of hydrogel with the substrate.

Figure 2C:
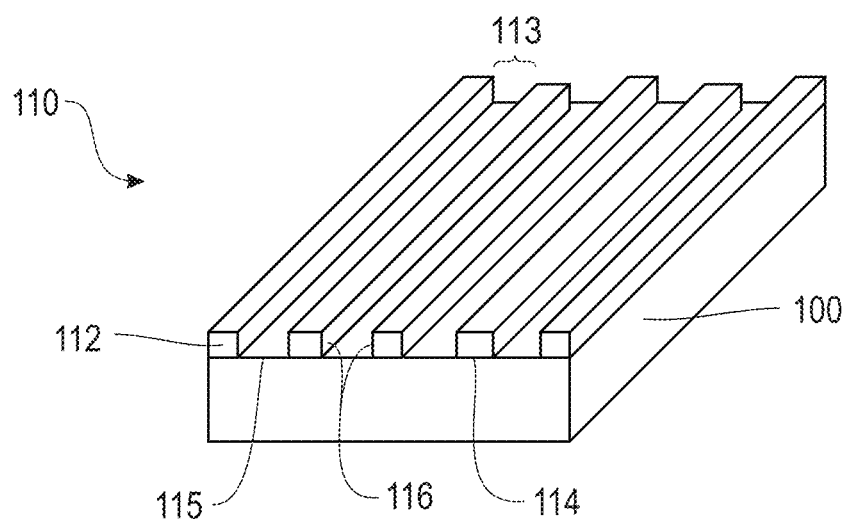

The following example (FIGS. 2A-2G) illustrates the formation of an exemplary 3-dimensional layered structure by direct-write printing the composition onto regions of a substrate surface. FIG. 2A (cross-sectional layer diagram) shows substrate 100 having print surface 101. The regions of print surface 101 are controlled by a CAD/CAM software program operating in a computer, which is in communication with the direct-write printer (not shown). In this instance, the printer has an extruding print-head operating at a temperature of about 15° C. to about 45° C. The printer "ink" is a disclosed thermo-responsive shear-thinning composition. At these temperatures and at a concentration of about 10-30 wt % TBC based on total weight of the composition, preferably 10-20 wt % TBC, the composition is a self-supporting gel in the absence of a shear force. Under high shear conditions of the extruding print-head, the composition is a free-flowing liquid. For purposes of illustration, the print nozzle of this example has a square-shaped opening (not shown). The print nozzle opening can be any suitable shape.

In a first pass of the print-head, square shaped strands of the composition are extruded from the print nozzle onto various regions of print surface 101. The strands rapidly gain viscosity after exiting the print nozzle due to the zero shear (or near zero shear) conditions of the substrate surface, resulting in the strands having substantially the same shape and dimensions as the print nozzle opening. Completion of the first pass results in layered structure 110 (FIG. 2B, cross-sectional view). Layered structure 110 comprises patterned layer 111 comprising square-shaped strands 112 disposed on substrate surface regions 114. The strands are separated by recessed areas 113 bounded by sidewalls 116 and substrate top surface 115. Substrate top surface 115 has substantially none of the composition disposed thereon. Strands 112 are in a self-supporting, non-crosslinked gelled state due to the absence of a shear stress outside the print-head. FIG. 2C is an overhead perspective of layered structure 110 showing patterned layer 111.

Figure 2D:
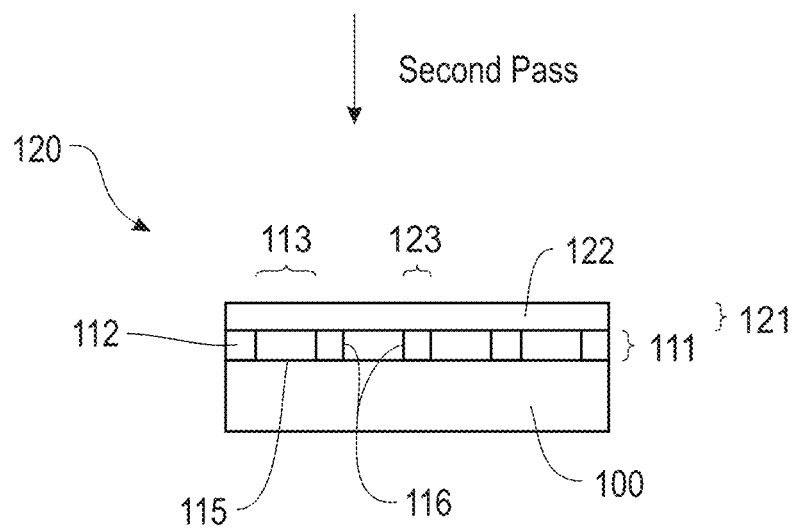
Figure 2E:
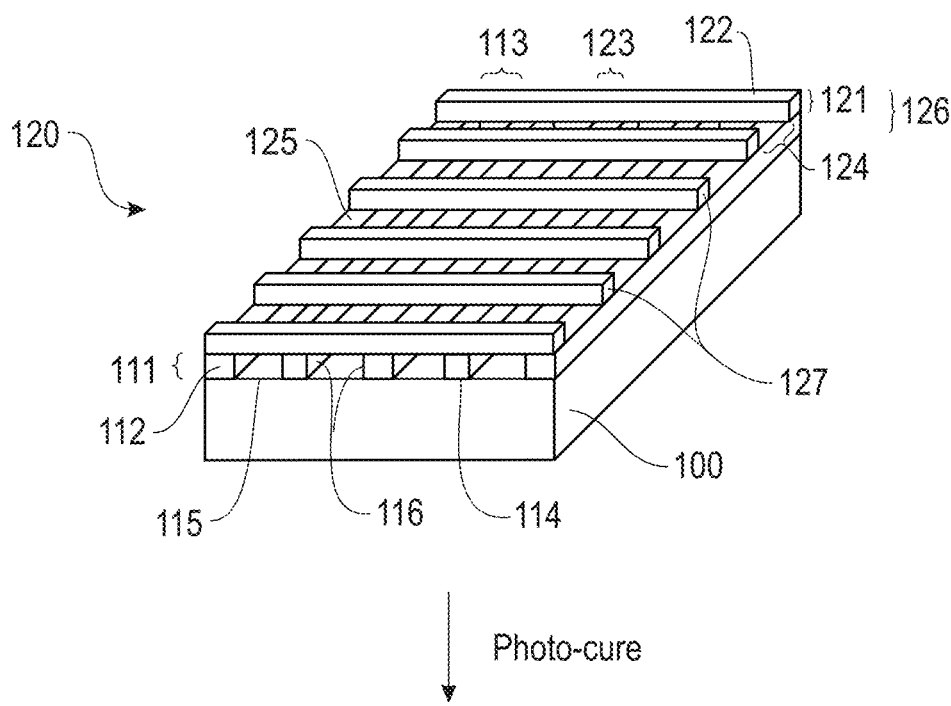
Figure 2F:
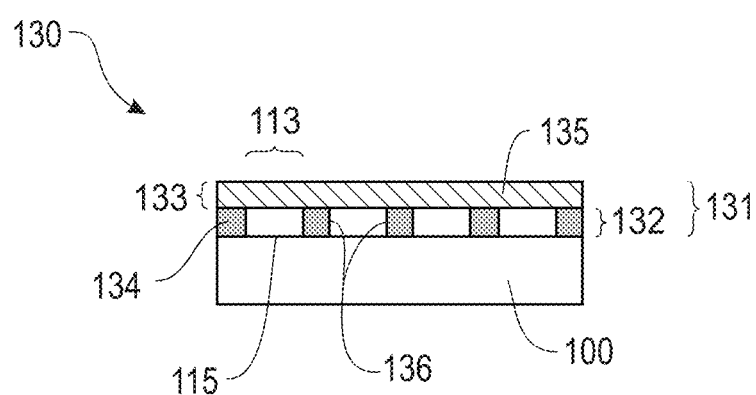

The final layered structure can have one or more layers. For illustration purposes, the final layered structure of this example has a stack comprising 2 layers of crisscrossed parallel spaced strands of the composition disposed on substrate 100. A second pass of the print-head forms layered structure 120 (FIG. 2D, cross-sectional view). Structure 120 comprises patterned layer 121 comprising square-shaped strands 122 disposed on patterned layer 111. Strands 122 are oriented orthogonal to strands 112, and make contact with strands 112 only at overlap areas 123. Strands 122 are in a gelled state, self-supporting, and non-crosslinked. FIG. 2E is an overhead perspective of structure 120 showing a 2-layered stack 126 comprising patterned layer 121 and patterned layer 111. Strands 122 of patterned layer 121 are disposed on and oriented orthogonal to strands 112 of patterned layer 111. Recessed areas 124 between strands 122 include sidewalls 127 of strands 122, exposed top surface 125 of strands 112, and substrate top surface 115. Strands 122 and strands 112 can partially fuse at overlap areas 123.

Layered structure 120 represents an initial structure comprising non-crosslinked triblock copolymer of the composition. The initial structure can comprise a stack of one or more patterned layers (e.g., a layer having topographical variation) and/or non-patterned layers (e.g., a planar film having uniform thickness). Preferably, the initial structure has a temperature above the sol-gel transition temperature of the composition and therefore is a self-supporting gel. The initial structure can have any shape and dimensions within the capability of the direct-write printer. Patterned layers can have any suitable pattern within the capability of the direct-write printer. Topographical features of a patterned layer can have any shape, dimensions, and/or contouring within the capability of the printer and the intended three-dimensional structure.

Following printing, the initial structure (e.g., structure 120) is preferably submitted to a photo-cure process for forming a final structure comprising crosslinked TBC. The photo-cure process comprises flood-exposing the initial structure to light of a wavelength effective in crosslinking the triblock copolymer of the initial structure by way of the above-described thiol-ene reaction. Preferably, the flood-exposure utilizes a source emitting at a wavelength of 300-450 nm. A particularly preferred ultraviolet wavelength is 310 nm. The duration time of the flood-exposure depends on the intensity of the light source. In general, the duration time can be 1 second to about 24 hours, 1 second to 5 hours, or more preferably 1 minute to 1 hour. The curing process can be performed at a temperature between 0° C. and about 45° C., preferably about 15° C. to about 30° C., at which temperature the initial structure is in a gelled state.

Figure 2G:
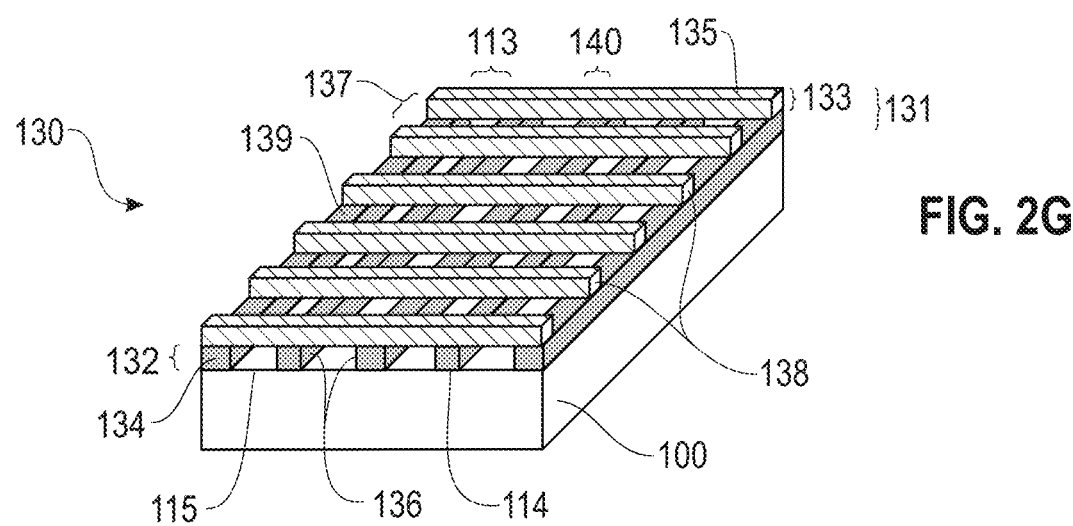

To illustrate, submitting structure 120 to a photo-cure process produces structure 130 (FIG. 2F), a crosslinked 2-layered structure. Structure 130 comprises stack 131 comprising crosslinked patterned layer 132 disposed on crosslinked patterned layer 133, which are derived from patterned layer 111 and patterned layer 121, respectively. Crosslinked patterned layer 132 comprises square-shaped crosslinked strands 134 derived from strands 112. Crosslinked patterned layer 133 comprises square-shaped crosslinked strands 135 derived from strands 122. Crosslinked strands 134 have sidewalls 136, which are substantially perpendicular to a main plane of surface 115. That is, the crosslinked strands have substantially the same shape and dimensions as the opening of the print nozzle. FIG. 2G is an overhead perspective of structure 130 showing 2-layered stack 131 comprising crosslinked patterned layer 133 disposed on crosslinked patterned layer 132. Crosslinked strands 135 of patterned layer 133 are disposed on and oriented orthogonal to crosslinked strands 134 of crosslinked patterned layer 132. Recessed areas 137 between crosslinked strands 135 include sidewalls 138 of crosslinked strands 135, exposed top surface 139 of crosslinked strands 134, and substrate top surface 115. Crosslinked strands 135 can be covalently bound to crosslinked strands 134 at overlap areas 140.

The final layered structure can be used for tissue engineering and for in vitro and in vivo cell cultures. The layered structure can comprise one or more printed patterned layers arranged in a stack. The printed patterned layers can fuse or otherwise combine. Alternatively, the layers can remain substantially separate and divided. If desirable, the stack of cured printed patterned layers can be separated from the substrate.

Each printed layer can have a thickness of about 2 micrometers to about 3 millimeters, and more particularly about 20 micrometers to about 100 micrometers.

The substrate can have a planar or non-planar print surface for deposition of strands and/or microdrops of the composition. Planar substrate surfaces include film sheets, paper sheets, glass plates, metal foils, and the like. Non-planar substrate surfaces can have topographical features of varying height, width, and contouring (e.g., a bone surface).

Substrates can comprise living and non-living materials. Exemplary non-limiting substrate materials include synthetic polymer (e.g., polycarbonate, polyester, polystyrene, polyurethane, poly(meth)acrylate, polysiloxane), plant and/or animal tissues (cartilage, bone, skin, kidney, pancreas, liver, cellulose fiber), glass (e.g., silicon dioxide), metal (e.g., aluminum, steel, tin, tungsten, titanium, silver, gold, zinc), ceramic, and carbide.

The printer can be any suitable direct-write printer comprising a dispensing head capable of controlled extrusion of strands or ejection of microdrops of the composition. The print-head reservoir can have a temperature below or above the sol-gel transition temperature of the composition, preferably a temperature of about 15° C. to about 45° C. The viscosity of the composition at the dispensing head can be about 0.5 to about 50 centipoise, preferably about 1 to about 20 centipoise, and even more preferably about 1 to about 10 centipoise.

The strand size of the composition depends on the diameter of the printer nozzle and the print speed. A given strand can have a cross-sectional area of about 10 to about 200 square micrometers.

A given microdrop can have a volume of about 0.5 to about 500 picoLiters, preferably 5 to 100 picoLiters, and more preferably 10 to 75 picoLiters.

The initial layered structure can be formed using two or more passes of the print-head over a given print surface area of the substrate, the print-head delivering one or more strands or microdrops per pass to a given surface area in accordance with instructions from a computer.

The printing surface temperature is preferably above the sol-gel transition temperature of the composition, preferably about 15° C. to about 45° C., and most preferably about 15° C. to about 25° C. At these surface temperatures, the strands or microdrops of the initial structure are in a gelled state comprising non-crosslinked composition.

In an embodiment, the initial structure comprises at least one living cell.

The printing device can include a two-dimensional (X-Y) or three-dimensional (X-Y-Z) plotter (e.g., driven by the step motors). The print-head can be mounted over an X-Y-Z plotter to allow precise deposition of strands or microdrops onto the print surface. Positioning of the X-Y-Z plotter under the print-head can be controlled via a controller, which can acquire the positioning information from a computer program in communication with the printer or through direct controller commands.

The print-head can comprise one or more independent nozzles. A given nozzle can have a diameter between 0.05 and 500 micrometers, between 0.5 and 100 micrometers, between 10 and 70 micrometers, or preferably between 20 and 60 micrometers. More preferably, each nozzle has a diameter of about 40 or 50 micrometers for ejecting microdrops. The dispensing head can dispense one or more simultaneous strands and/or microdrops. The direct write printer can comprise a plurality of nozzles having the same or different diameters. A given nozzle opening can have any suitable shape (e.g., circular, oval, square, rectangular, pentagonal, hexagonal).

Ink-Jet Printing

The thermo-responsive properties of the compositions allow the compositions to be used as a liquid ink in an ink-jet print-head operating at a temperature of between 0° C. and about 8° C. Upon contact with a substrate surface having a temperature of about 15° C. to about 45° C., the printed droplets heat-thicken to form a non-crosslinked gel disposed on the substrate. The ink-jetted initial structure can be photo-crosslinked as described above.

Molding the Composition

The thermo-responsive properties also allow the compositions to be molded as a liquid at a temperature between 0° C. and about 10° C. Heating the molded liquid reversibly generates a self-supporting non-crosslinked molded gel structure. The molded gel structure can be photo-crosslinked as described above.

The following examples demonstrate the preparation of the compositions and their use in a direct-write printing process to form a crosslinked multi-layered structure after photo-curing.

EXAMPLES

Materials used in the following examples are listed in Table 1.

TABLE 1

| ABBRE-VIATION | DESCRIPTION | SUPPLIER |
|---|---|---|
| | IRGACURE 2959 | BASF |
| | DAROCUR 1173 | BASF |
| AGE | Allyl glycidyl ether | Sigma-Aldrich |
| DCM | Dichloromethane | Sigma-Aldrich |
| DEE | Diethyl ether | Sigma-Aldrich |
| DTT | Dithiothreitol | Sigma-Aldrich |
| F127 | PLURONIC F-127, Mn 12,000 | BASF |
| iPrGE | Isopropyl glycidyl ether | Sigma-Aldrich |
| MeO-PEG-SH | Methoxy-poly(ethylene glycol)-thiol $M_n$ 800 | Sigma-Aldrich |
| $P_4$-t-Bu | 1-tert-Butyl-4,4,4-tris(dimethylamino)-2,2-bis[tris(dimethylamino)-phosphoranylidenamino]-2$\lambda$5,4$\lambda$5-catenadi(phosphazene), about 0.8M in hexane | Sigma-Aldrich |
| PEG | Poly(ethylene glycol) Mn 8,000 | Sigma-Aldrich |
| PETMP | Pentaerythritol tetrakis (3-mercaptopropionate) | Sigma-Aldrich |
| Tol | Toluene | Sigma-Aldrich |
| TSB | Tryptic Soy Broth, DIFCO ™ | Becton, Dickinson and Company |

Herein, Mn is the number average molecular weight, Mw is the weight average molecular weight, and MW is the molecular weight of one molecule.

The following materials were purchased.

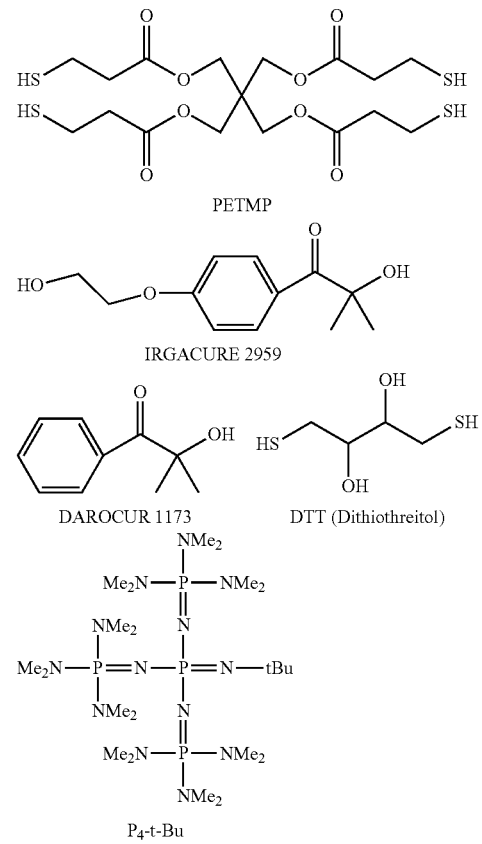

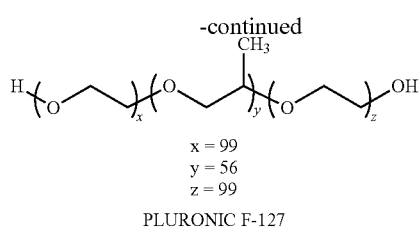

x = 99
y = 56
z = 99

PLURONIC F-127

Triblock Polymer Preparation

Example 1

Synthesis of triblock copolymer, TBC-1 (iPrGE:AGE 90:10 m/m):

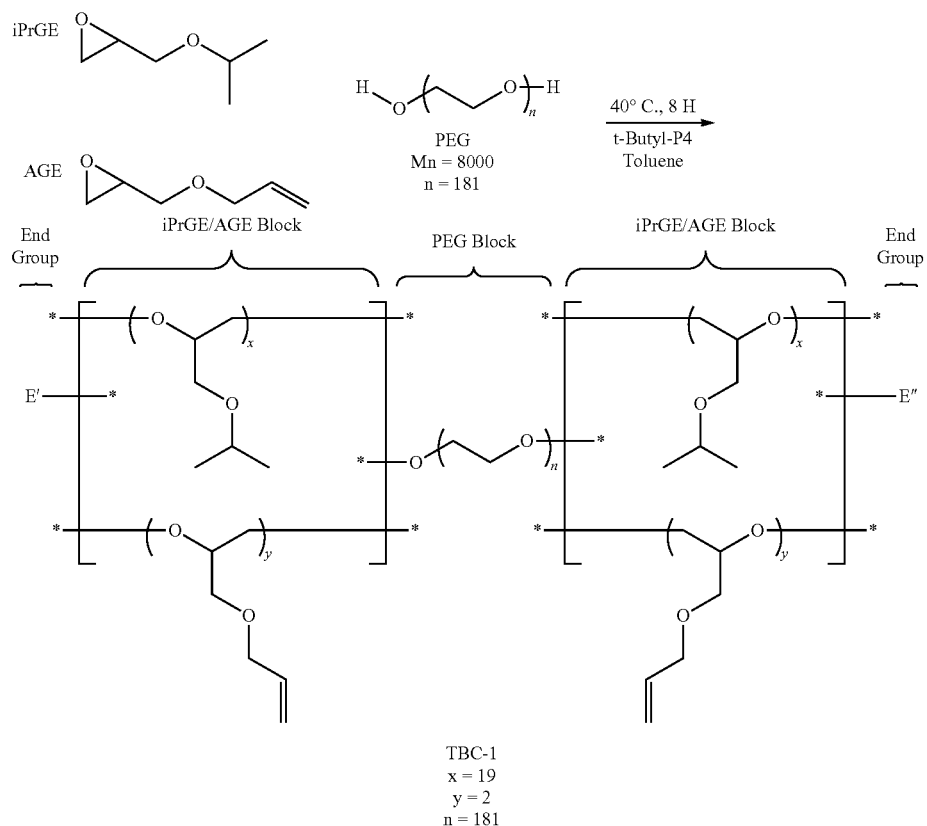

TBC-1
x = 19
y = 2
n = 181

In the above structure of TBC-1, each iPrGE/AGE block is enclosed in square brackets. Vertical stacking of the iPrGE and AGE repeat units within the square brackets indicates a random distribution of these repeat units within the block. The iPrGE/AGE blocks are linked together by a central PEG block. End groups E' and E" can be any suitable end group. In this instance, E' and E" are hydrogen, and each iPrGE/AGE block has a living chain end (alcohol —OH group).

Figure 3:
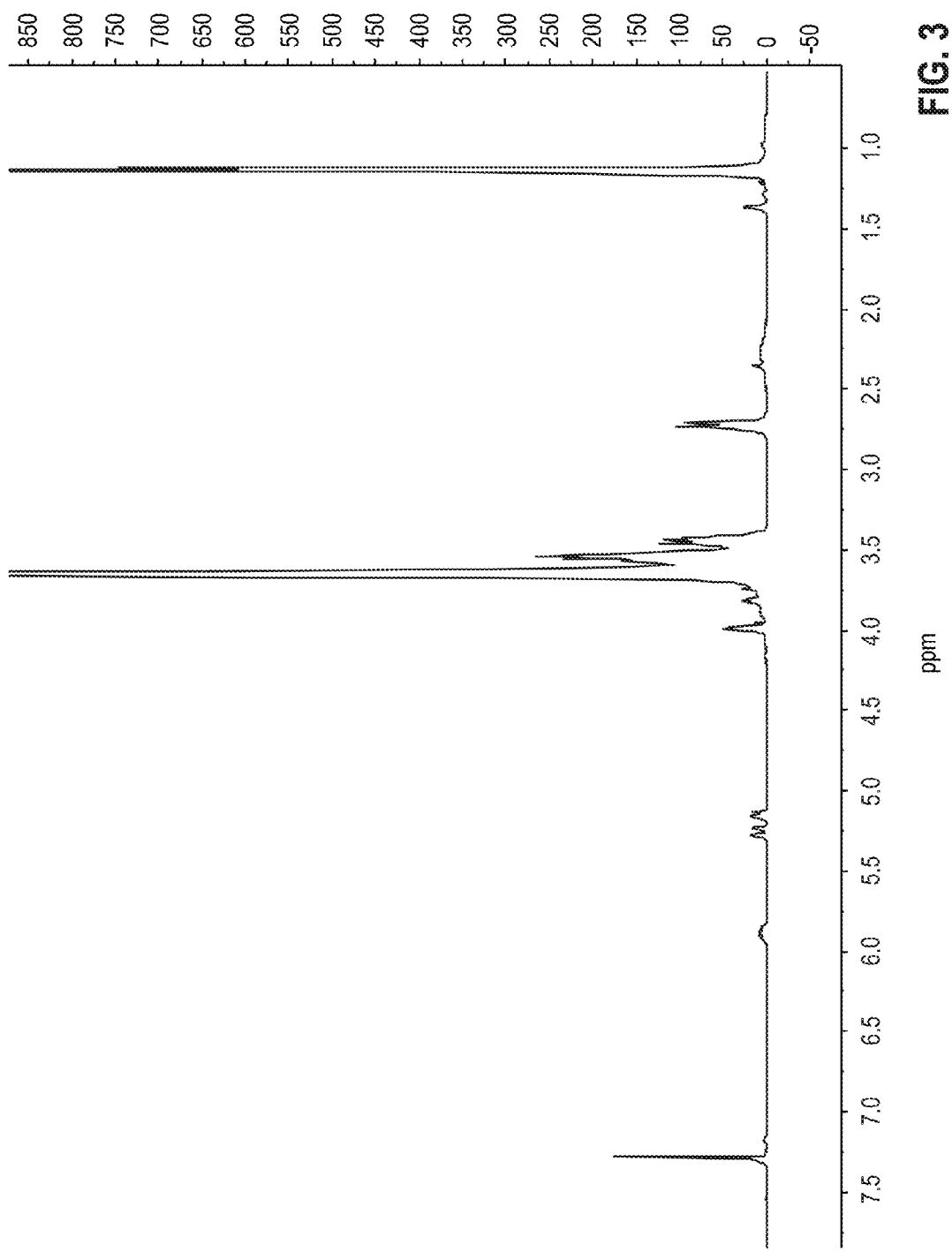
FIG. 3 is a $H^1$ NMR spectrum of triblock copolymer TBC-1.

Triblock copolymer TBC-1 was prepared in a glove box using the following procedure. Poly(ethylene glycol) (10.0 g, Mn=8000, 1 molar equivalent (mol eq)) and toluene (33 mL) were combined in a dry 100-mL, round-bottomed flask. The mixture was heated and stirred until dissolved. Isopropylglycidyl ether (iPrGE, 7.84 g, 67.5 mol equivalents, MW 116.2) and allyl glycidyl ether (AGE, 1.075 g, 7.5 mol equivalents, MW 114.1) were added and the reaction mixture was allowed to stir until homogeneous. Organocatalyst $P_4$-t-Bu (1.56 mL, 0.33 mol eq/OH, solution in hexane) was added and the reaction mixture was stirred at 45° C. for 8 hours. An aliquot was sampled at the end of the reaction to ensure no unreacted epoxide monomer remained. The solution was quenched with methanol (3 mL) and the polymer was precipitated into diethyl ether. The polymer was collected via centrifugation (4.4 rpm, 4° C., 10 minutes), and the supernatant was disposed. The polymer was redissolved in a minimal amount of dichloromethane and precipitated into diethyl ether (repeated twice). The polymer was redissolved into dichloromethane and passed through a 0.25 micrometer filter, concentrated, and dried at 40° C. under vacuum (10 mm Hg). $^1$H NMR was used to confirm the structure of the polymer (FIG. 3, NMR spectrum, 300 MHz, 25° C., $CDCl_3$). Mn (NMR)=12,800, where each iPrGE/AGE block had an Mn=2400 (x=19, y=2 in the above structure) and the PEG block had an Mn=8000 (n=181 in the above structure). For purposes of calculating the amount of crosslinking agent and photoinitiator in the following examples, 1 mole of TBC-1=12800 g based on Mn, and contained 4 allyl groups.

Example 1A

Synthesis of triblock copolymer, TBC-2 (iPrGE:AGE 75:25 m/m). This polymer was prepared as Example 1 using an iPrGE:AGE ratio of 75:25 m/m.

Example 1B

Synthesis of triblock copolymer, TBC-3 (iPrGE:AGE 50:50 m/m). This polymer was prepared as Example 1 using an iPrGE:AGE ratio of 75:25 m/m.

Example 1C

Synthesis of triblock copolymer, TBC-4 (iPrGE:AGE 100:0 m/m). This polymer was prepared as Example 1 using an iPrGE:AGE ratio of 100:0 m/m.

Figure 4:
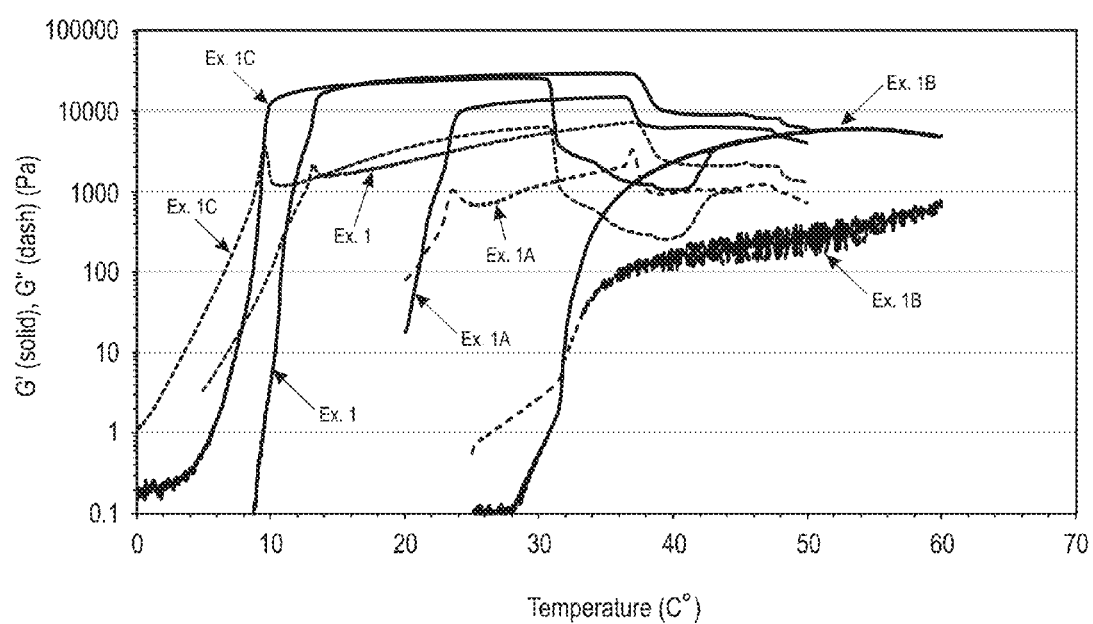
FIG. 4 is a graph showing the temperature dependence of the storage modulus (G', solid line) and loss modulus (G", dashed line) of Examples 1, 1A, 1B and 1C.

Aqueous solutions were prepared of Examples 1, 1A, 1B, and 1C at 15 wt % in polymer. The solutions of Examples 1, 1A, and 1B formed gels at 25° C., whereas Example 1C formed a gel only upon heating to 32° C. The temperature dependence of the storage (G') and loss (G") moduli are shown graphically in FIG. 4. The storage modulus G' is shown as a solid line, and the loss modulus G" is shown as a dashed line.

Figure 5:
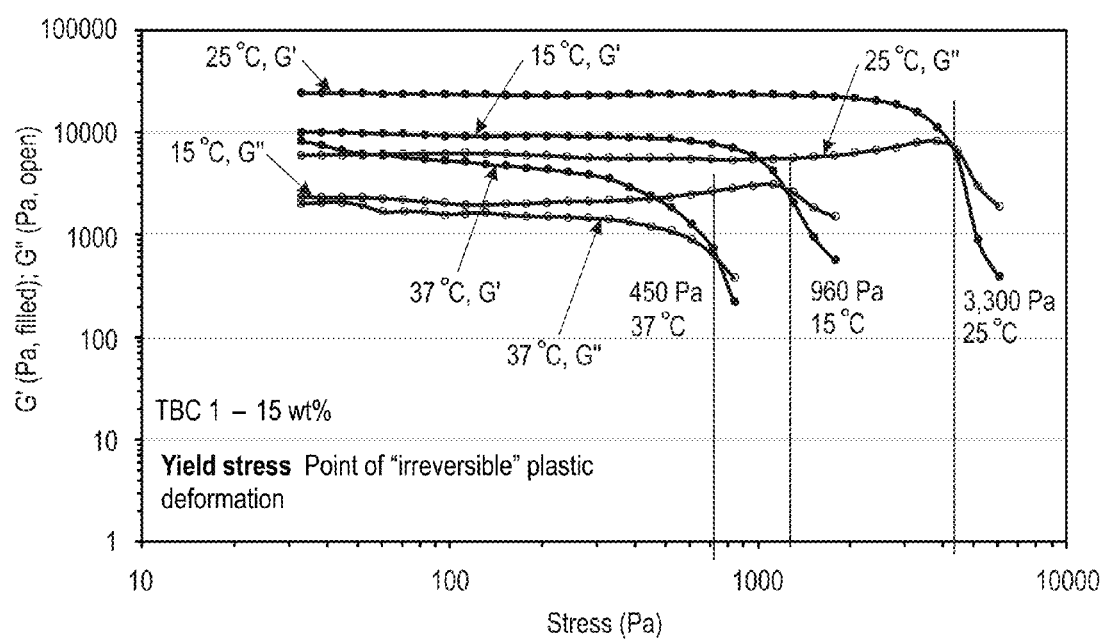
FIG. 5 is a graph showing the yield stress properties of the 15 wt % solution of TBC-1 at temperatures of 15° C., 25° C., and 37° C. The highest yield stress (3300 Pa) was obtained at 25° C.

FIG. 5 is a graph showing the yield stress properties of the 15 wt % solution of TBC-1 at temperatures of 15° C., 25° C., and 37° C. The highest yield stress (3300 Pa) was obtained at 25° C.

Figure 6:
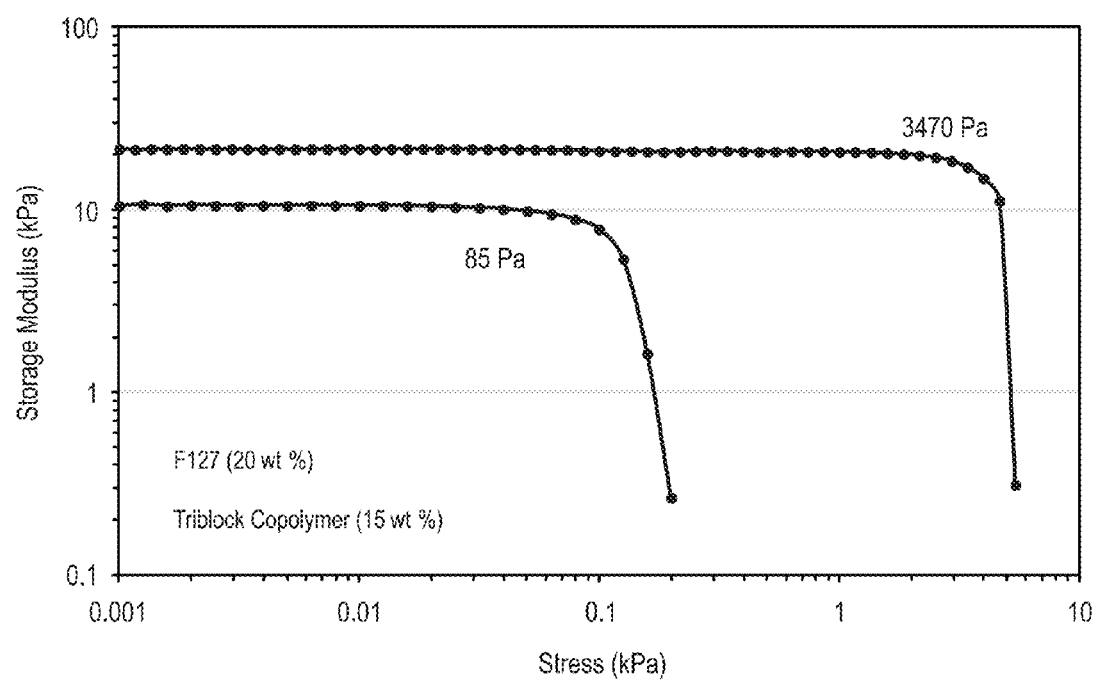
FIG. 6 is a graph comparing the gel strength and yield stress properties of the 15 wt % solution of TBC-1 and a 20 wt % solution of PLURONIC F-127 at temperatures of 25° C.

FIG. 6 is a graph comparing the gel strength and yield stress properties of the 15 wt % solution of TBC-1 and a 20 wt % solution of F-127 at temperatures of 25° C. The yield stress of TBC-1 was 3470 Pa and F-127 was 85 Pa. Thus, non-crosslinked TBC-1 provides a stronger gel at lower concentration compared to non-crosslinked F-127.

Hydrogel Formulations

Example 2 (Comparative)

Preparation of hydrogel formulation HF-1 using a water insoluble multifunctional thiol crosslinker PETMP and a photoinitiator. The following procedure serves as an example for a hydrogel formulation containing 13-15 wt % TBC-1 based on total weight of the formulation. The triblock copolymer TBC-1 (0.4122 g, 0.032 mmol, containing 0.128 mmol allyl groups) was combined with water (2.74 g). The mixture was stirred at ice bath temperature for at least 1 day or until the hydrogel was completely homogenous. The crosslinker PETMP (17.2 mg, 0.141 mmol, 1.1 mol equivalent relative to allyl units) was added as a liquid to the mixture and stirred for 3 hours at ice bath temperature. In the cold, liquid state, the solution appeared homogenous. However in the gel state, it was evident the PETMP coalesced on the gel surface. The photoinitiator, IRGACURE 2959 (0.8 mg, 5 wt % relative to total weight of allyl monomer AGE in the polymer), was added to the mixture and stirred at ice bath temperature for 15 minutes.

Example 3 (Comparative)

Preparation of hydrogel formulation HF-2. This formulation was prepared using the general procedure of Example 2, substituting IRGACURE 2959 with DAROCUR 1173 (0.8 mg, 5 wt % relative to allyl group).

Example 4 (Comparative)

Preparation of hydrogel formulation HF-3 using water soluble monofunctional thiol (MeO-PEG-SH). The following procedure serves as an example for the 15 wt % hydrogel formulation. The triblock copolymer (0.7755 g) was combined with water (4.39 g). The mixture was stirred at ice bath temperature for at least 1 day or until the hydrogel was completely homogenous. Mono-thiol MeO-PEG-SH (33.5 mg, 0.217 mmol, 1 mole equivalent relative to allyl units) was added to the mixture and stirred for 3 hours at ice bath temperature. The photoinitiator, DAROCUR 1173 (1.24 mg, 5 wt % relative to allyl group) was added to the mixture and stirred at ice bath temperature for 15 minutes.

Example 5 (Comparative)

Preparation of hydrogel formulation HF-4 using water soluble monofunctional thiol (MeO-PEG-SH). This formulation was prepared using the general procedure of Example 4, substituting DAROCUR 1173 with IRGACURE 2959 (1.2 mg, 5 wt % relative to allyl group).

Example 6

Preparation of hydrogel formulation HF-5 using water soluble multifunctional thiol crosslinker (DTT). The following procedure serves as an example for the 15 wt % hydrogel formulation. The triblock copolymer (0.7755 g) was combined with water (4.39 g). The mixture was stirred at ice bath temperature for at least 1 day or until the hydrogel was completely homogenous. The crosslinker, DTT (33.5 mg, 0.217 mmol, 1 mol eq relative to allyl units), was added to the mixture and stirred for 3 hours at ice bath temperature. The photoinitiator, DAROCUR 1173 (1.24 mg, 5 wt % relative to allyl group) was added to the mixture and stirred at ice bath temperature for 15 minutes.

Example 7

Preparation of hydrogel formulation HF-6 using water soluble multifunctional thiol crosslinker (DTT). This formulation was prepared using the general procedure of Example 6, substituting DAROCUR 1173 with IRGACURE 2959 (1.2 mg, 5 wt % relative to allyl group).

Example 8

Preparation of hydrogel formulation HF-7 using water soluble multifunctional thiol crosslinker (DTT). This formulation was prepared using the general procedure of Example 6 using DAROCUR 1173 (0.7 mg, 3 wt % relative to allyl group).

Example 9

Preparation of hydrogel formulation HF-8 using water soluble multifunctional thiol crosslinker (DTT). This formulation was prepared using the general procedure of Example 6 using DAROCUR 1173 (0.2 mg, 1 wt % relative to allyl group).

Example 10 (Comparative)

Preparation of hydrogel formulation HF-9 without a crosslinking agent. This formulation was prepared using the general procedure of Example 6 omitting the DTT, and using DAROCUR 1173 (1.2 mg, 5 wt % relative to allyl group).

Example 11 (Comparative)

Preparation of a 15 wt % PLURONIC F127 solution, PL-1. PL-1 was prepared by combining F127 (1.0 g) with water (5.7 g) and stirring the mixture 1 day at ice bath temperature or until the polymer solution was completely homogeneous.

Example 12 (Comparative)

Preparation of a 20 wt % PLURONIC F127 solution, PL-2. PL-2 was prepared using the procedure of Example 33, F127 (1.0 g), and water (4.0 g).

Example 13 (Comparative)

Preparation of hydrogel formulation HF-10, a 15 wt % TBC-1 solution. HF-10 was prepared using the procedure of Example 33, TBC-1 (0.5 g), and water (2.87 g).

Example 14 (Comparative)

Preparation of hydrogel formulation HF-11, a 20 wt % TBC-1 solution. HF-11 was prepared using the procedure of Example 33, TBC-1 (0.7 g), and water (2.8 g).

Table 2 summarizes the hydrogel formulations.

UV Curing Experiments

Examples 15-36

The following procedure was used to characterize the crosslinking sensitivity of the hydrogel formulations to exposure with 310 nm ultraviolet (UV) light without patterning. A hydrogel formulation was poured as a cold liquid into a glass or aluminum dish and covered with a glass slide to reduce potential evaporation. The sample was cured under 310 nm UV light for various times at room temperature or at 5° C. The crosslinking success was evaluated qualitatively by placing the pan on an ice bath to observe the sol-gel transition. Covalent crosslinking produced a clear, elastic, free-standing film that was stable at ice bath temperature and room temperature (i.e., the gel exhibited no sol-gel transition), whereas a non-crosslinked material was a clear flowing liquid at ice bath temperature and was a gel at room temperature (r.t., about 20-23° C.)

The gel fraction was determined by drying a UV-treated film in a vacuum oven at 100 mm Hg at 40° C. for 1 day, and extracting the dried film overnight with dichloromethane (DCM) using a Soxhlet extractor. The gel fraction of the initial dried UV treated film was calculated from the formula listed below:

Gel Fraction=(initial dry film mass−final dry film mass)/(initial dry film mass)×100%

Table 3 summarizes the 310 nm UV curing experiments of Examples 15-37.

TABLE 2

| Example | Hydrogel Formulation Name | Polymer | Polymer (g) | Water (g) | Thiol Name | Thiol (mg) | Thiol water soluble? | Photo-initiator (PI) | PI (mg) | Total Wt (g) | PI[a] (wt %) | Polymer[b] (wt %) |
|---|---|---|---|---|---|---|---|---|---|---|---|---|
| 2 (comp) | HF-1 | TBC-1 | 0.41 | 2.74 | PETMP | 17.2 | N | IRGACURE 2959 | 0.66 | 3.17 | 5 | 13.0 |
| 3 (comp) | HF-2 | TBC-1 | 0.41 | 2.74 | PETMP | 17.2 | N | DAROCUR 1173 | 0.66 | 3.17 | 5 | 13.0 |
| 4 (comp) | HF-3 | TBC-1 | 0.78 | 4.39 | MeO-PEG-SH | 33.5 | Y | DAROCUR 1173 | 1.24 | 5.20 | 5 | 14.9 |
| 5 (comp) | HF-4 | TBC-1 | 0.78 | 4.39 | MeO-PEG-SH | 33.5 | Y | IRGACURE 2959 | 1.24 | 5.20 | 5 | 14.9 |
| 6 | HF-5 | TBC-1 | 0.78 | 4.39 | DTT | 33.5 | Y | DAROCUR 1173 | 1.24 | 5.20 | 5 | 14.9 |
| 7 | HF-6 | TBC-1 | 0.78 | 4.39 | DTT | 33.5 | Y | IRGACURE 2959 | 1.24 | 5.20 | 5 | 14.9 |
| 8 | HF-7 | TBC-1 | 0.78 | 4.39 | DTT | 33.5 | Y | DAROCUR 1173 | 0.74 | 5.20 | 3 | 14.9 |
| 9 | HF-8 | TBC-1 | 0.78 | 4.39 | DTT | 33.5 | Y | DAROCUR 1173 | 0.25 | 5.20 | 1 | 14.9 |
| 10 (comp) | HF-9 | TBC-1 | 0.78 | 4.39 | | 0 | | DAROCUR 1173 | 1.24 | 5.17 | 5 | 15.0 |
| 11 (comp) | PL-1 | F127 | 0.80 | 4.56 | | 0 | | | 0 | 5.36 | | 15.0 |
| 12 (comp) | PL-1 | F127 | 0.71 | 2.83 | | 0 | | | 0 | 3.54 | | 20.0 |
| 13 (comp) | HF-10 | TBC-1 | 0.58 | 3.28 | | 0 | | | 0 | 3.85 | | 15.0 |
| 14 (comp) | HF-11 | TBC-1 | 0.51 | 2.04 | | 0 | | | 0 | 2.55 | | 20.0 |

[a]PI wt % is based on total weight of allyl monomer used to make the polymer.
[b]Polymer wt % is based on total weight of the formulation.

TABLE 3

| Example | Hydrogel Formu-lation | Polymer[b] (wt %) | Thiol | Thiol water soluble? | # of Thiol groups | Photoinitiator (PI) | PI (wt %)[a] | 310 nm Cure Time (min) | 310 nm Cure Temp (° C.) | Sol Gel Transition after cure?[c] | Gel Fraction (wt %) |
|---|---|---|---|---|---|---|---|---|---|---|---|
| 15 (comp) | HF-1 | 13.0 | PETMP | N | 4 | IRGACURE 2959 | 5 | 3 | 5 | Yes | 0 |
| 16 (comp) | HF-1 | 13.0 | PETMP | N | 4 | IRGACURE 2959 | 5 | 5 | 5 | Yes | 0 |
| 17 (comp) | HF-1 | 13.0 | PETMP | N | 4 | IRGACURE 2959 | 5 | 60 | 5 | Yes | 0 |
| 18 (comp) | HF-2 | 13.0 | PETMP | N | 4 | DAROCUR 1173 | 5 | 60 | 5 | Yes | 0 |
| 19 (comp) | HF-3 | 14.9 | MeO-PEG-SH | Y | 1 | DAROCUR 1173 | 5 | 3 | 5 | Yes | 0 |
| 20 (comp) | HF-3 | 14.9 | MeO-PEG-SH | Y | 1 | DAROCUR 1173 | 5 | 60 | 5 | Yes | 0 |
| 21 (comp) | HF-4 | 14.9 | MeO-PEG-SH | Y | 1 | IRGACURE 2959 | 5 | 60 | 5 | Yes | 0 |
| 22 | HF-5 | 14.9 | DTT | Y | 2 | DAROCUR 1173 | 5 | 10 | 5 | No | >88 |
| 23 | HF-5 | 14.9 | DTT | Y | 2 | DAROCUR 1173 | 5 | 3 | 5 | No | >88 |
| 24 | HF-6 | 14.9 | DTT | Y | 2 | IRGACURE 2959 | 5 | 10 | 5 | No | >88 |
| 25 | HF-7 | 14.9 | DTT | Y | 2 | DAROCUR 1173 | 3 | 20 | 5 | No | >88 |
| 26 | HF-7 | 14.9 | DTT | Y | 2 | DAROCUR 1173 | 3 | 15 | 5 | No | >80 |
| 27 | HF-7 | 14.9 | DTT | Y | 2 | DAROCUR 1173 | 3 | 10 | 5 | No | >80 |
| 28 | HF-7 | 14.9 | DTT | Y | 2 | DAROCUR 1173 | 3 | 5 | 5 | No | 0 |
| 29 | HF-7 | 14.9 | DTT | Y | 2 | DAROCUR 1173 | 3 | 3 | 5 | No | 0 |
| 30 | HF-8 | 14.9 | DTT | Y | 2 | DAROCUR 1173 | 1 | 20 | 5 | Yes | 88 |
| 31 | HF-8 | 14.9 | DTT | Y | 2 | DAROCUR 1173 | 1 | 15 | 5 | Yes | 86 |
| 32 | HF-8 | 14.9 | DTT | Y | 2 | DAROCUR 1173 | 1 | 12 | 5 | Yes | 84 |
| 33 | HF-8 | 14.9 | DTT | Y | 2 | DAROCUR 1173 | 1 | 10 | 5 | No | 0 |
| 34 | HF-8 | 14.9 | DTT | Y | 2 | DAROCUR 1173 | 1 | 5 | 5 | No | 0 |
| 35 | HF-5 | 14.9 | DTT | Y | 2 | DAROCUR 1173 | 5 | 3 | 25 | Yes | >88 |
| 36 (comp) | HF-9 | 15.0 | — | — | — | DAROCUR 1173 | 5 | 0 | No cure | Yes | 0 |
| 37 (comp) | HF-10 | 15.0 | — | — | — | — | — | — | — | Yes | 0 |

[a]PI wt % is based on total weight of allyl monomer used to make the polymer.
[b]Polymer wt % is based on total weight of the formulation.
[c]Yes = not effectively crosslinked (undesirable). No = effectively crosslinked (desirable)

The data of Table 3 demonstrate the following samples did not crosslink: Examples 15-18 containing a multi-functional water-insoluble thiol, Examples 19-21 containing a mono-functional water-soluble thiol, Example 36 containing no thiol crosslinking agent, and Example 37 having no thiol and no photoinitiator.

Figure 7A:
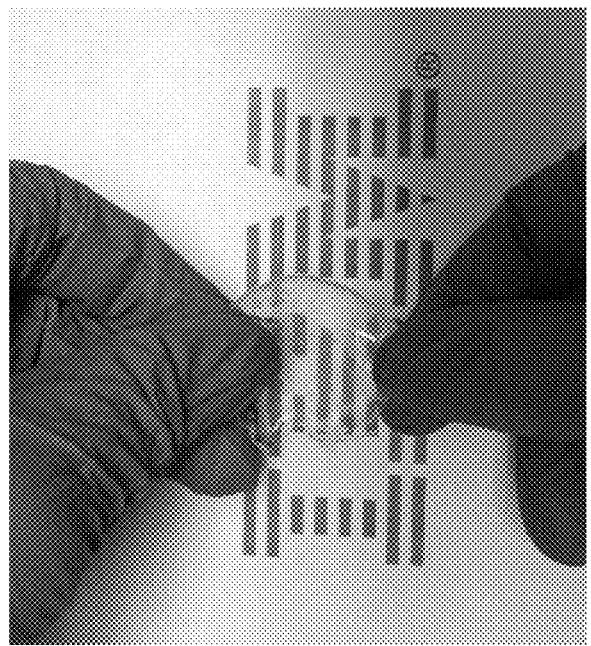
FIGS. 7A-7B are photographs of the non-patterned crosslinked film obtained in Example 23 using formulation HF-5.
Figure 7B:
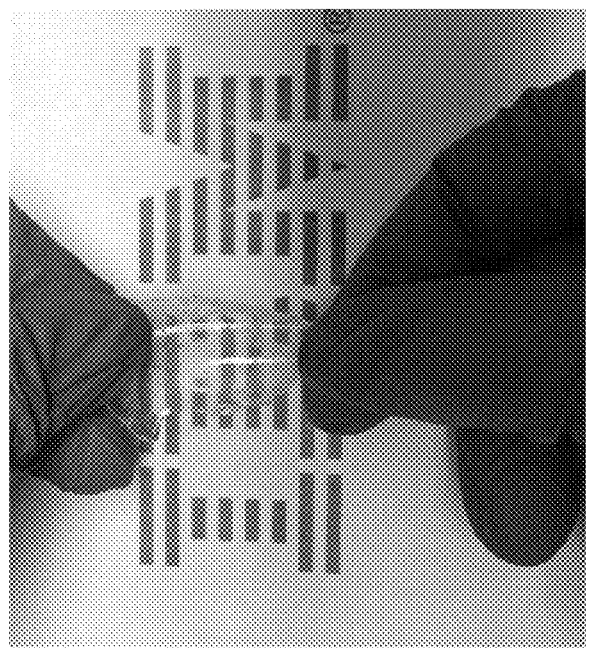

Samples that contained a multifunctional, water-soluble thiol and photoinitiator (Examples 22-27, 30-32 and 35) crosslinked when cured for a suitable time by 310 nm UV exposure. For the crosslinking samples, a gel fraction in a range of 80-88 wt % was obtained when the concentration of the photoinitiator was 1-5 wt % and the curing time was 3-20 minutes. FIGS. 7A and 7B are photographs of the unpatterned crosslinked film of Example 23. The film is clear, colorless, elastic and free-standing. FIG. 7A shows the unstretched film. FIG. 7B shows the stretched film.

The rate of crosslinking was affected by the photoinitiator concentration. At 5 wt % photoinitiator (Examples 22-24), exposure times of 3-10 minutes were effective in producing a gel fraction of >80%. At 3 wt % photoinitiator (Examples 25-29), an exposure time of about 10 minutes was needed to achieve 80% gel fraction (Example 27). At 1 wt % photoinitiator (Examples 30-34), an exposure time of about 12 minutes was needed to achieve 84% gel fraction (Example 32). Although curing times increased using the lower photoinitiator levels, the storage shelf-life and stability of the direct-write ink increased (desirable).

Table 3 also shows the effect of curing temperature on the gel fraction obtained. Formulation HF-5 was able to crosslink to produce a gel fraction of >88 wt % using a 3 minute curing time at 5° C. or 25° C. (compare Examples 23 and 35), which are below and above the sol-gel transition temperature of 10° C., respectively. Therefore, the cure can be performed on the liquid (pre-patterned) state and/or on the solid (patterned) state. The cure can be performed using a constant temperature or a temperature program involving two or more temperatures.

Evaluation of Gel Mechanical Properties Using Rheology

Dynamic oscillatory experiments were performed on a TA instrument AR-2000ex equipped using a 25 mm parallel plate geometry. Samples that were equilibrating in an ice bath for at least 10 minutes were carefully loaded onto the Peltier plate at 5° C. A pre-shear experiment was applied to ensure bubbles were eliminated from the sample cell, and a solvent trap was utilized to minimize solvent evaporation. The sample was equilibrated at 20° C. for 8 minutes. Strain sweep experiments were performed, and all experiments were conducted using a strain value in the linear viscoelastic regime. Temperature ramp experiments were performed at an oscillating plate frequency of 1 Hz and a temperature ramp from 0-45° C. at 0.5° C./min.

Figure 8:
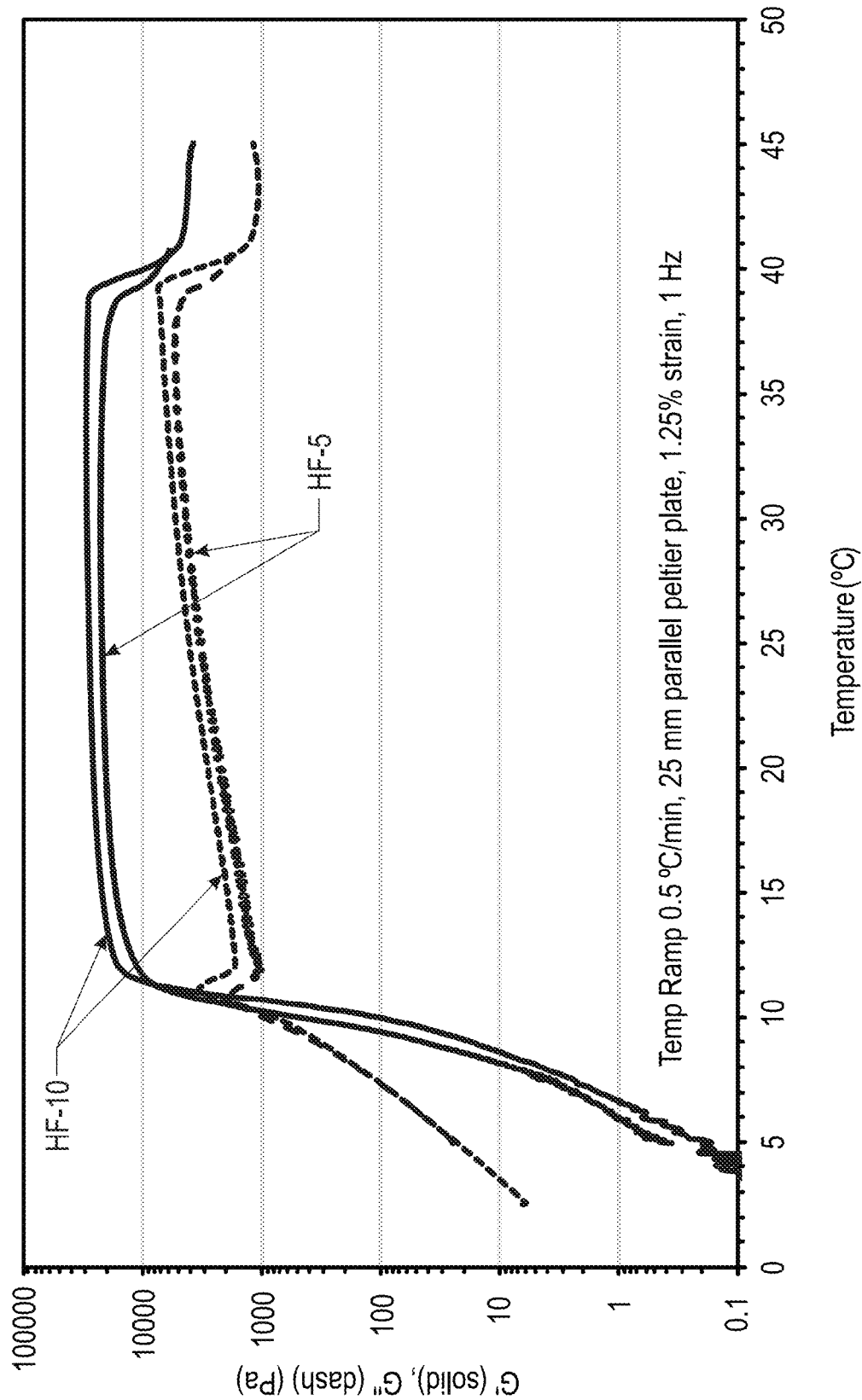
FIG. 8 is a graph showing the temperature dependence of the storage modulus (G') and loss modulus (G") of hydrogel mixtures HF-5 (with crosslinking agent and photoinitiator) and HF-10 (without crosslinking agent and photoinitiator), using an oscillating plate frequency of 1 Hz and a temperature ramp of 0-45° C. at 0.5° C./min.

The temperature dependence of the storage modulus (G') and loss modulus (G") of hydrogel mixtures HF-5 (with crosslinking agent and photoinitiator) and HF-10 (without crosslinking agent and photoinitiator) were compared using the above frequency/temperature ramp conditions (FIG. 8, graph). The results show that each liquid solution at 5° C. underwent a sol-gel transition at about 10° C. and remained a gel when heated to the highest temperature of 45° C. No difference in the overall gel modulus or sol-gel transition was observed for these two samples.

Figure 9:
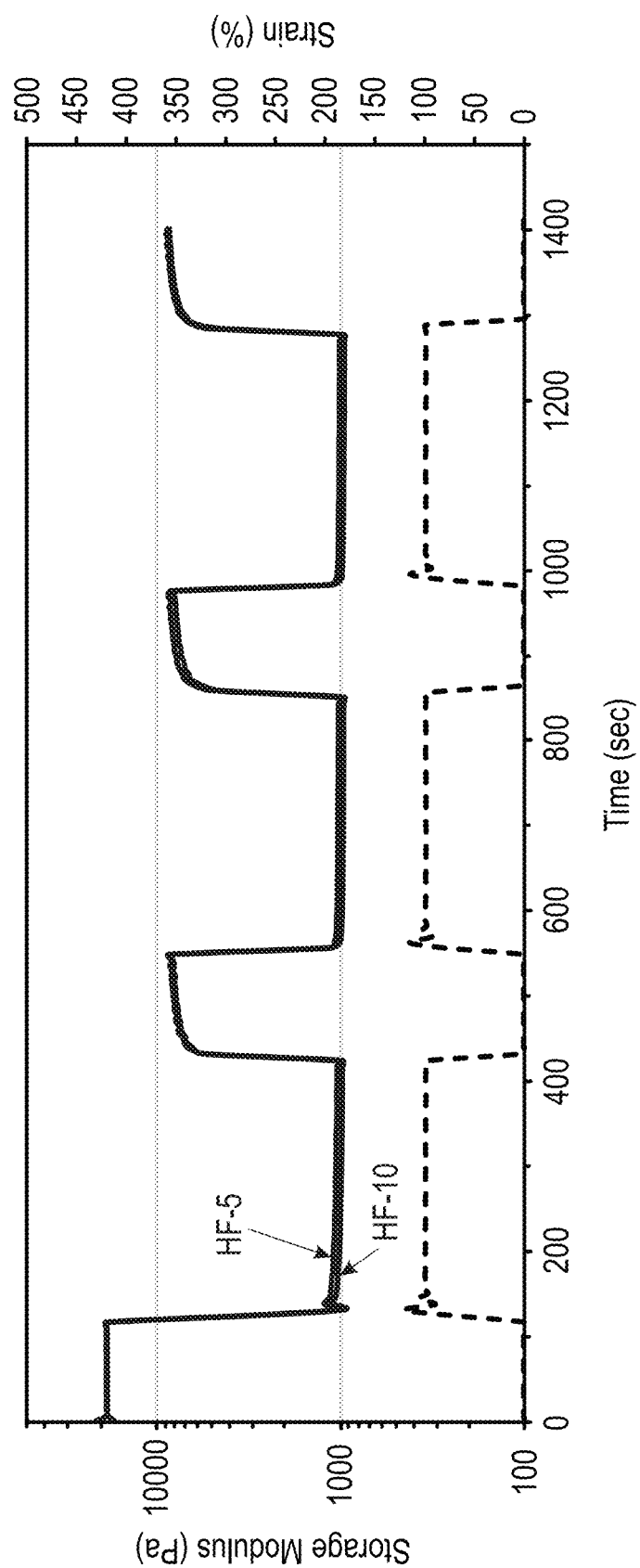
FIG. 9 is a graph showing the results of the cyclic strain experiments on hydrogel mixtures HF-5 and HF-10.

Cyclic strain experiments were conducted to investigate the shear-thinning and recovery behavior of the hydrogels. Samples were loaded on a 25 mm parallel plate geometry at 5° C. and a pre-shear experiment was performed to eliminate bubbles from the sample. Cyclic tests (frequency 1 Hz) were performed at 25° C. using alternating strains of 1% for 2 min and 100% for 5 minutes per a cycle. FIG. 9 (graph) shows the results of the cyclic strain experiments, which indicate no discernible difference in the modulus response to sustained 1% and 100% strains by HF-5 and HF-10. There was an instantaneous and reproducible storage modulus response to a change in strain. Minimal hysteresis was observed in the modulus after repetitive cyclic shearing.

Figure 10:
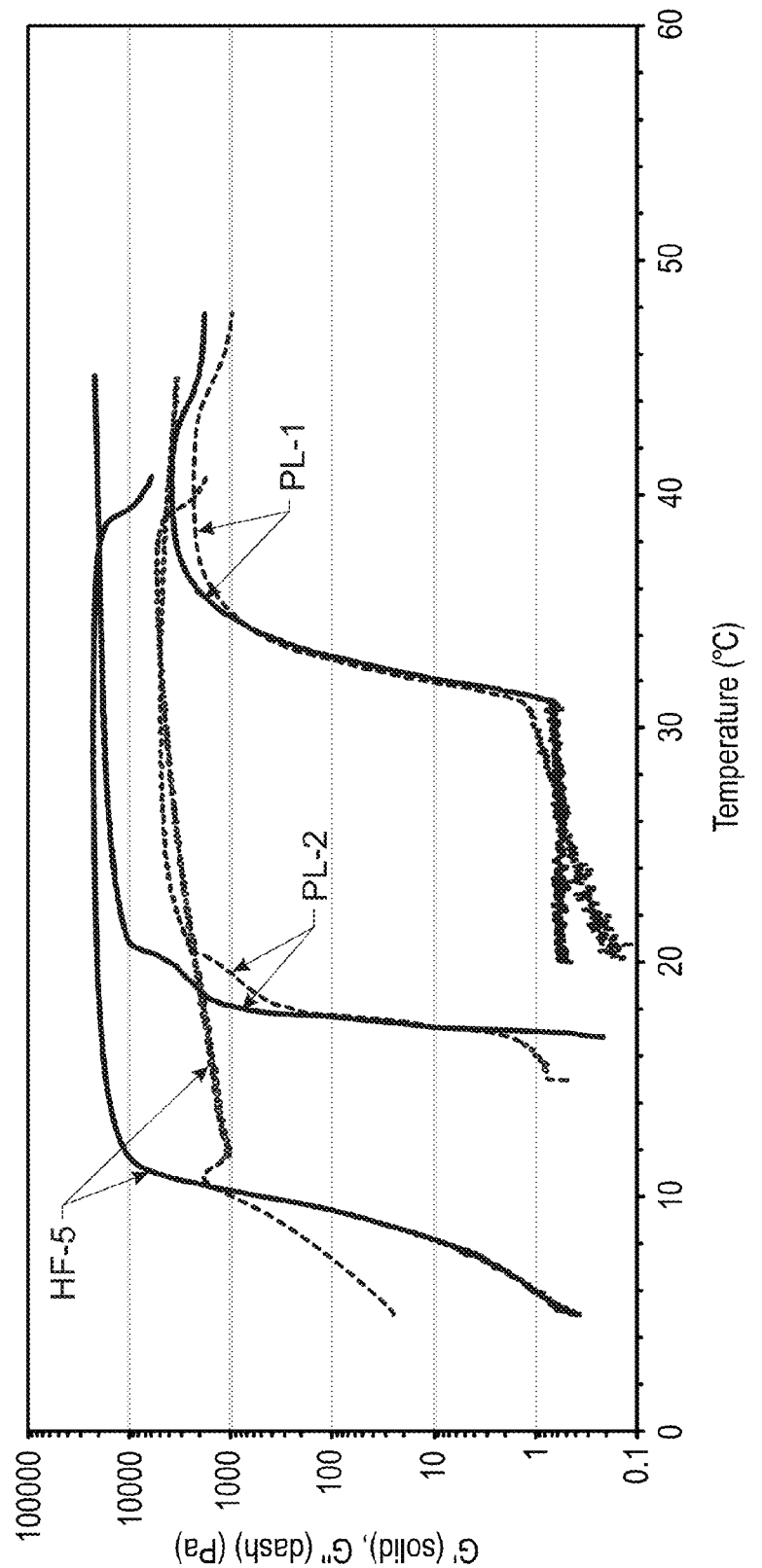
FIG. 10 is a graph comparing the temperature dependence of the storage modulus (G') and loss modulus (G") of hydrogel mixture HF-5 (with crosslinking agent and photoinitiator) and two solutions containing PLURONIC F127: PL-1 (15 wt % F-127) and PL-2 (20 wt % F-127), using an oscillating plate frequency of 1 Hz and a temperature ramp of 0-45° C. at 0.5° C./min.

Temperature ramp rheological experiments of formulation HF-5 was also evaluated and compared with PL-1 (15 wt % F127) and PL-2 (20 wt % F127), as shown in FIG. 10 (graph). The advantage of TBC-1 is in the improved mechanical properties compared to the commercially available F127 system. At identical wt % polymer, TBC-1 showed a lower gelation temperature and higher modulus than F127, which is a liquid at room temperature. Furthermore, it is necessary to use higher concentrations of F127 compared to TBC-1 to achieve similar modulus.

Figure 11:
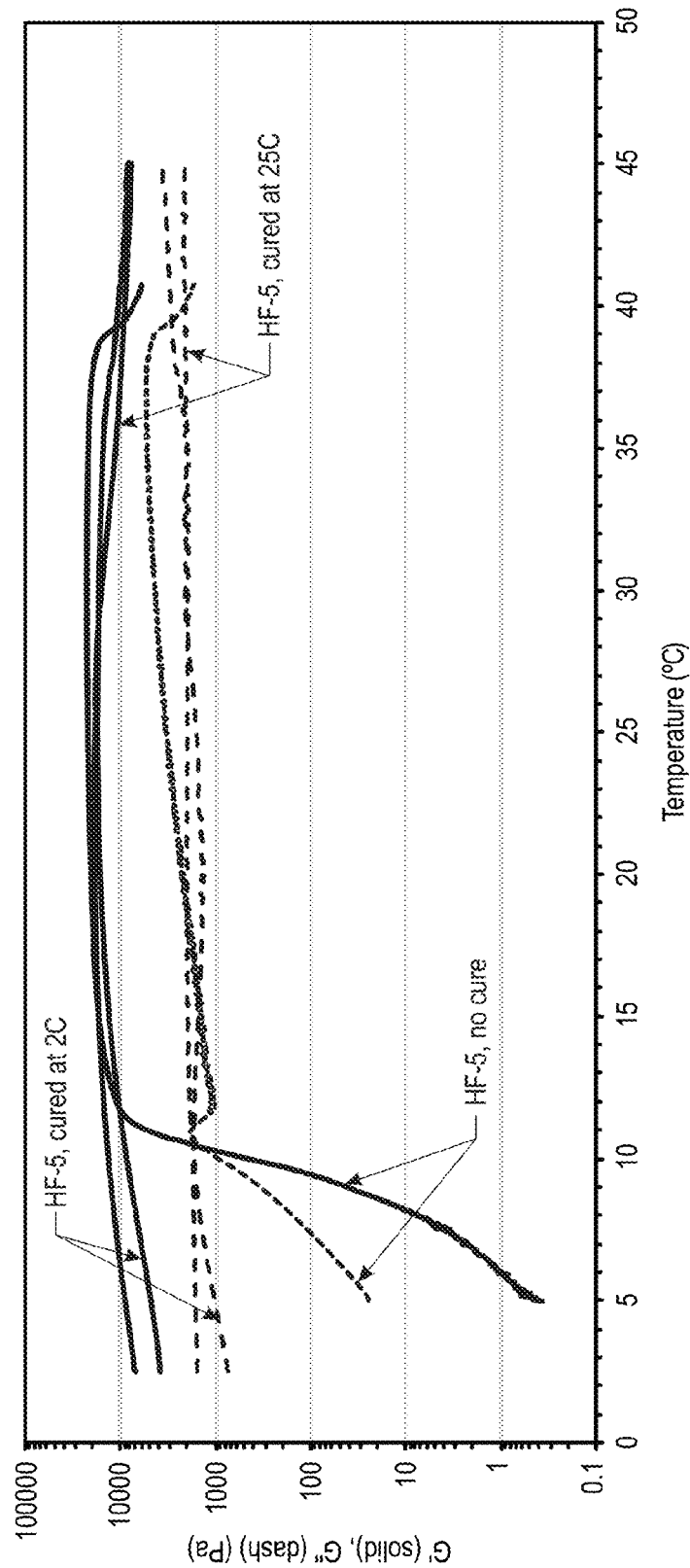
FIG. 11 is a graph comparing the temperature dependence of the storage modulus (G') and loss modulus (G") of hydrogel formulation HF-5 before curing, cured at 2° C., and cured at 25° C., using an oscillating plate frequency of 1 Hz and a temperature ramp of 0-45° C. at 0.5° C./min.

FIG. 11 is a graph comparing the temperature dependence of the storage modulus (G') and loss modulus (G") of hydrogel mixture HF-5 before curing, cured at 2° C., and cured at 25° C., using an oscillating plate frequency of 1 Hz and a temperature ramp of 0-45° C. at 0.5° C./min. The study shows the gels after UV curing no longer exhibit the sol-gel transition. Curing below or above the sol-gel transition did not affect the overall gel modulus or mechanical properties of the cured gels.

3-Dimensional (3D) Printing

A direct write printer was assembled from a three stepper motor stage which enabled the printer to translate in the x, y, and z directions at 10 micrometers resolution. The pressure was supplied using a NORDSON™ fluid dispenser and the stepper motor stage was controlled by a GALIL™ controller. The printer was controlled using a MATLAB® software. The 3D printable ink formulation, which as a liquid at 5° C. was poured into a NORDSON OPTIMUM® 3 mL fluid dispensing barrel equipped with a conical (diameter=100 micrometers) precision tip nozzle. The loaded barrel was capped and centrifuged at 4.4 rpm, 4° C., and 5 minutes to eliminate any bubbles that were trapped during ink loading. The cold ink in the barrel was equilibrated at room temperature for at least 5 minutes, forming a high viscosity shear-thinning gel. During printing, the ink is subjected to a high shear rate determined by the dispensing pressure. The high shear lowers the ink viscosity (lowers G') at the time of shear. The dispensed ink, which is not under shear, immediately returns to the high modulus state (a rigid gel) consistent with the stress profile of FIG. 6.

Various sized printing nozzles were tested with the ink composition. In this instance, conical nozzles produced better printed features compared to cylindrical nozzles.

Figure 12A:
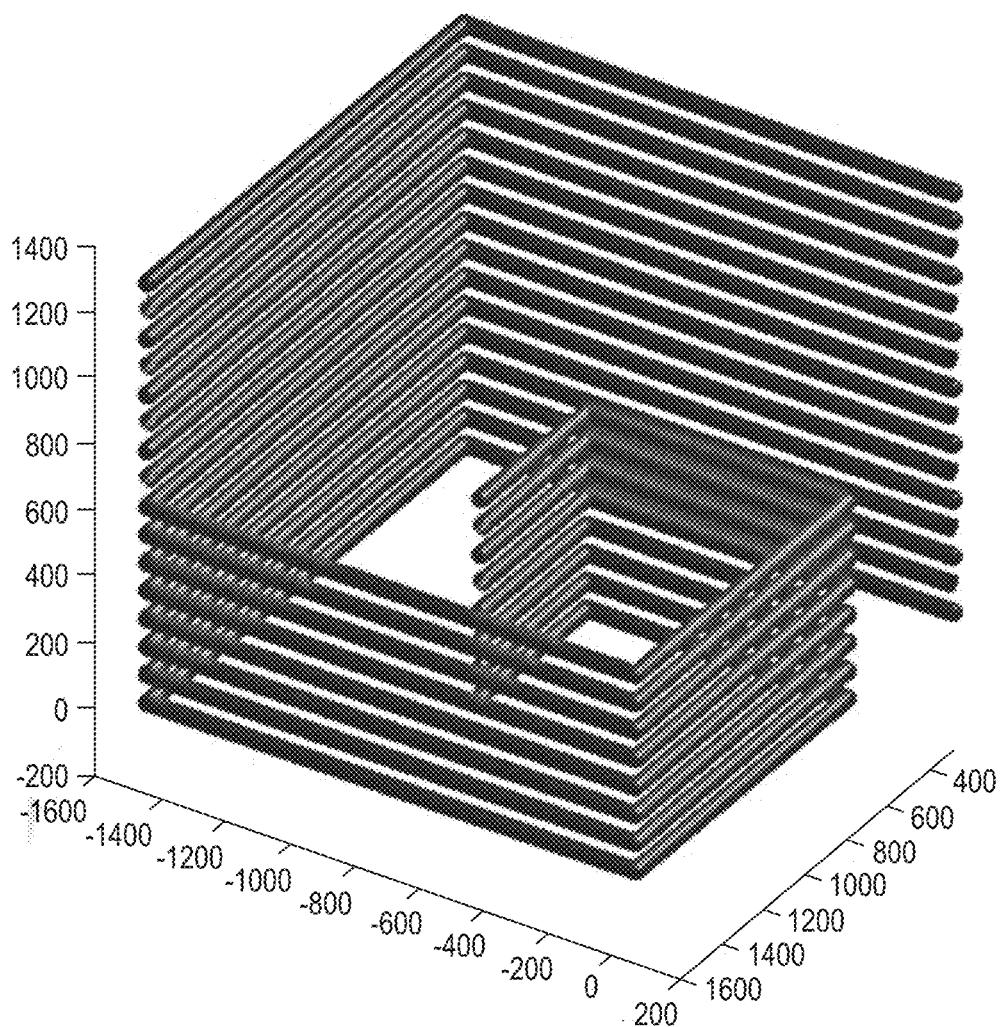
FIG. 12A is a drawing of a three-dimensional spiral target used for direct write printing tests.
Figure 12B:
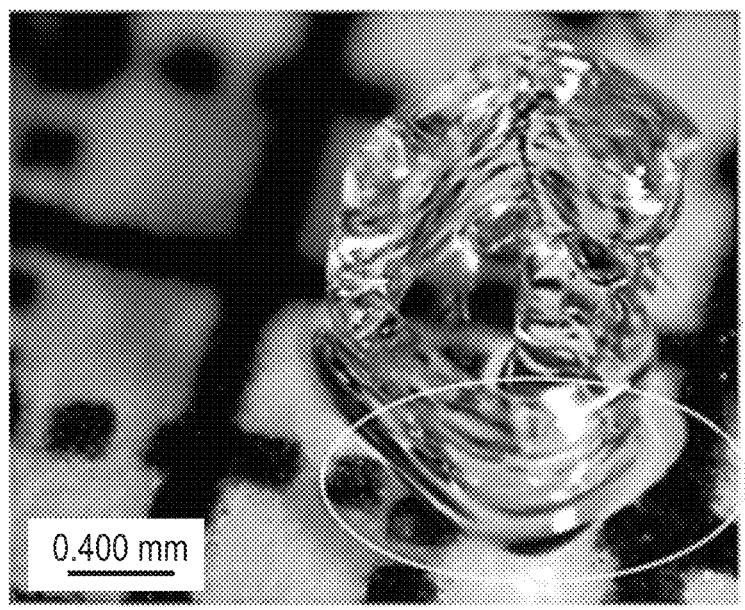
FIG. 12B is a photograph showing a plan view of the spiral target printed using a 30 wt % aqueous solution of PLURONIC F-127. The layered structure shows considerable sagging.
Figure 13A:
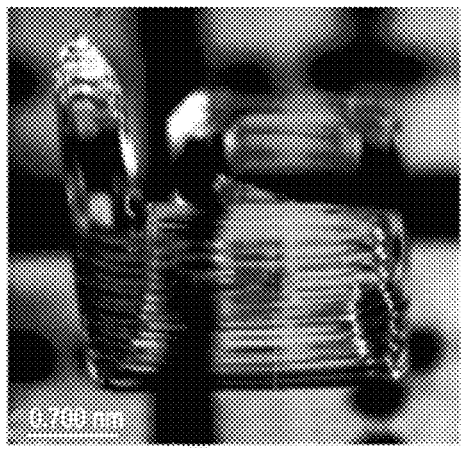
FIGS. 13A-13B are photographs showing a side view and an opposite side view, respectively, of the spiral target of FIG. 12A printed using a 16 wt % aqueous solution of TBC-1. The layered structure was self-supporting, showing minimal sagging.
Figure 13B:
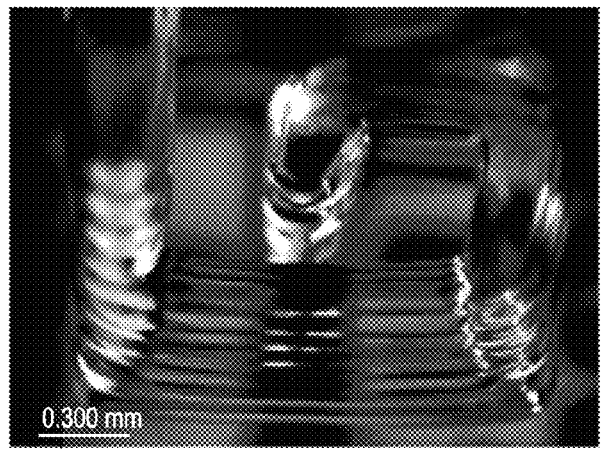

In a first direct write test, a three-dimensional stacked spiral target (FIG. 12A) was printed using the following conditions: a 50 micrometer conical nozzle, a speed of 125 micrometers/second, and a pressure of 50 psi. Under these conditions, a 30 wt % aqueous solution of PLURONIC F-127 produced the non-crosslinked spiral structure of FIG. 12B (photograph, plan view). A 16 wt % aqueous solution of TBC-1 produced the non-crosslinked spiral structure of FIGS. 13A (photograph, side view) and 13B (photograph, opposite side view). The spiral structure created with TBC-1 had good stability and regularity, whereas considerable sagging (circled) was observed with the F-127 solution.

Figure 14A:
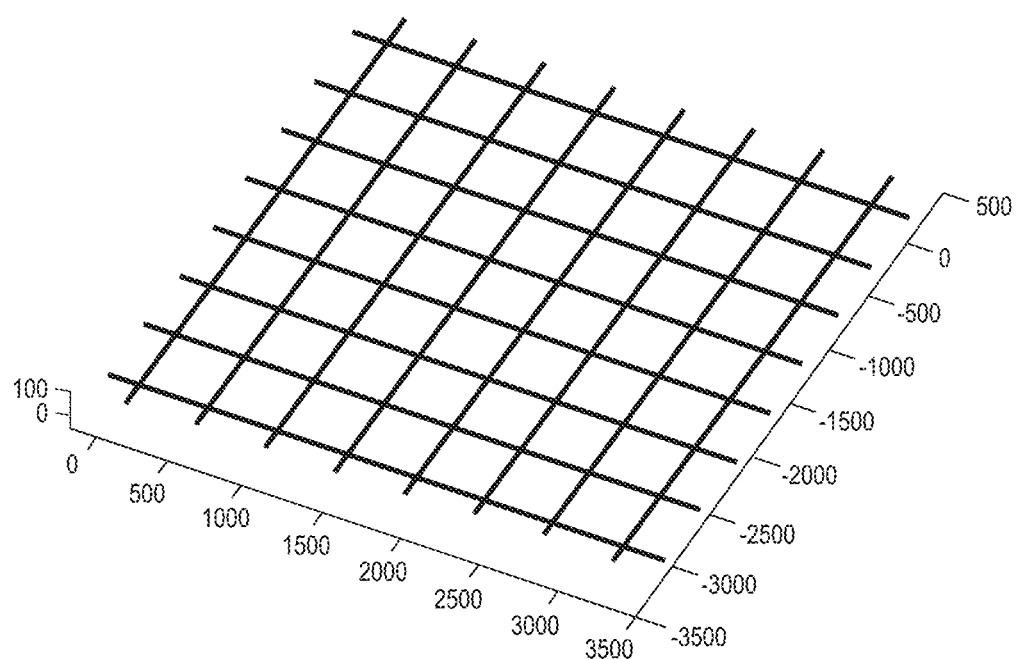
FIG. 14A is a drawing of a three-dimensional scaffold target used for direct write printing tests.
Figure 14B:
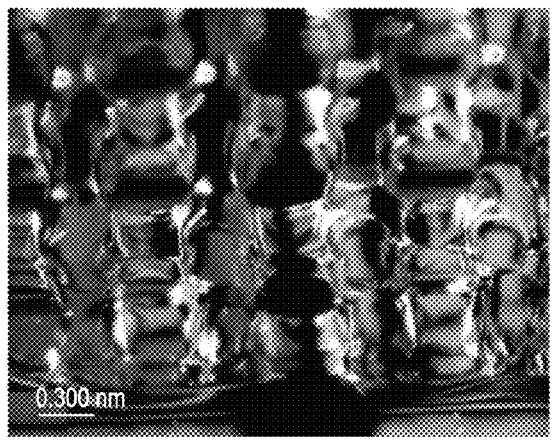
FIGS. 14B-14C are photographs showing a side view at two magnification levels of the scaffold target printed using a 30 wt % aqueous solution of PLURONIC F-127. Considerable sagging can be seen in non-overlapping areas of the scaffold.
Figure 14C:
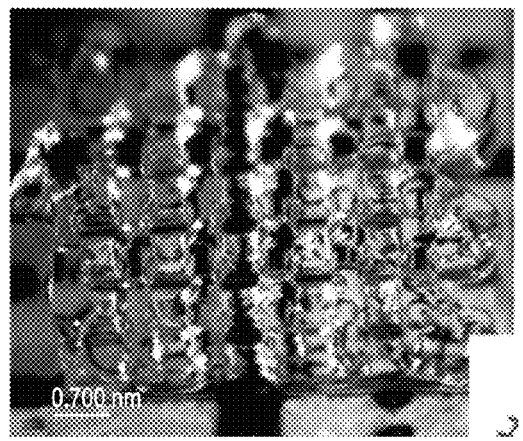
Figure 15A:
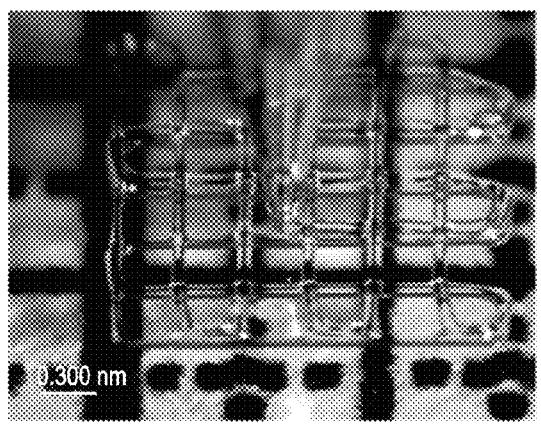
FIG. 15A is a photograph showing a plan view during printing of the scaffold target printed using a 16 wt % aqueous solution of TBC-1. Minimal sagging was observed.
Figure 15B:
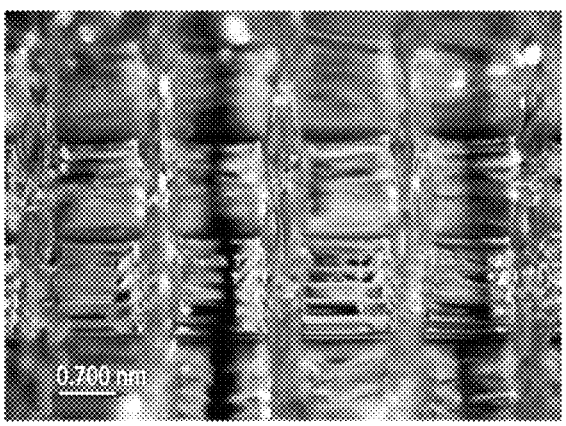
FIG. 15B is a photograph showing a plan view after printing the scaffold target printed using a 16 wt % aqueous solution of TBC-1.

In a second direct write test, a three dimensional scaffold target (FIG. 14A) was printed. A 30 wt % aqueous solution of PLURONIC F-127 produced the non-crosslinked scaffold of FIG. 14B (photograph, side view) and FIG. 14C (higher magnification) using a 100 micrometer conical nozzle, a speed of 175 micrometers/second, and a pressure of 10 psi. A 16 wt % aqueous solution of TBC-1 produced the non-crosslinked scaffold shown in FIG. 15A (photograph, plan view, during printing) and FIG. 15B (photograph, plan view, after printing). There was considerably more sag in the scaffold prepared with F-127.

Figure 16A:
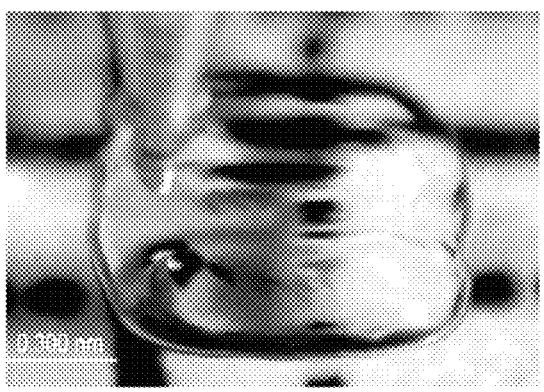
FIGS. 16A-16B are photographs of a printed resolution target comparing the resolution capability of a 23 wt % solution of F-127 to a 32 wt % solution of TBC-1, respectively.
Figure 16B:
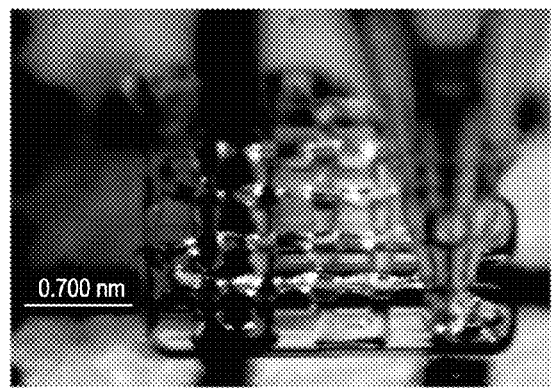

FIGS. 16A and 16B compare the resolution capability of a 23 wt % solution of F-127 to a 32 wt % solution of TBC-1, respectively, using a 50 micrometer conical nozzle and the same printed stacked structure.

Figure 17A:
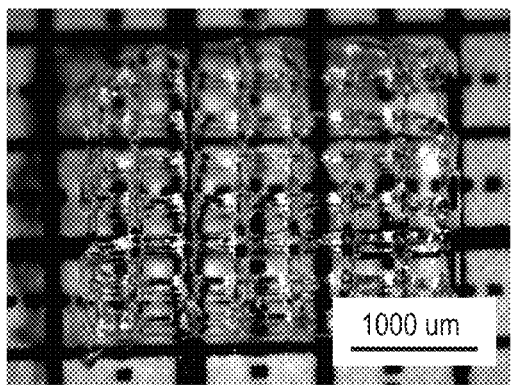
FIGS. 17A-17B are photographic images at two magnifications of a 3-D printed object before curing, obtained using formulation HF-5 with a 100 micrometer diameter conical nozzle operating at 25 psi. The printed 3-layered scaffold shows ordered and self-supporting features.
Figure 17B:
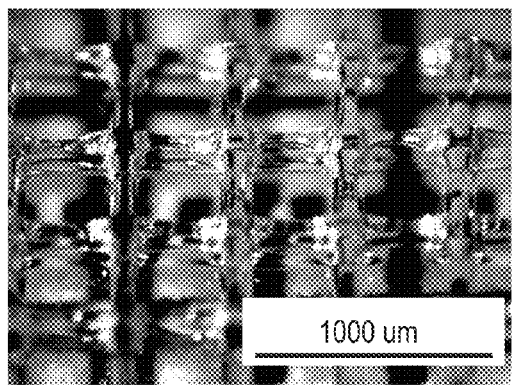
Figure 18:
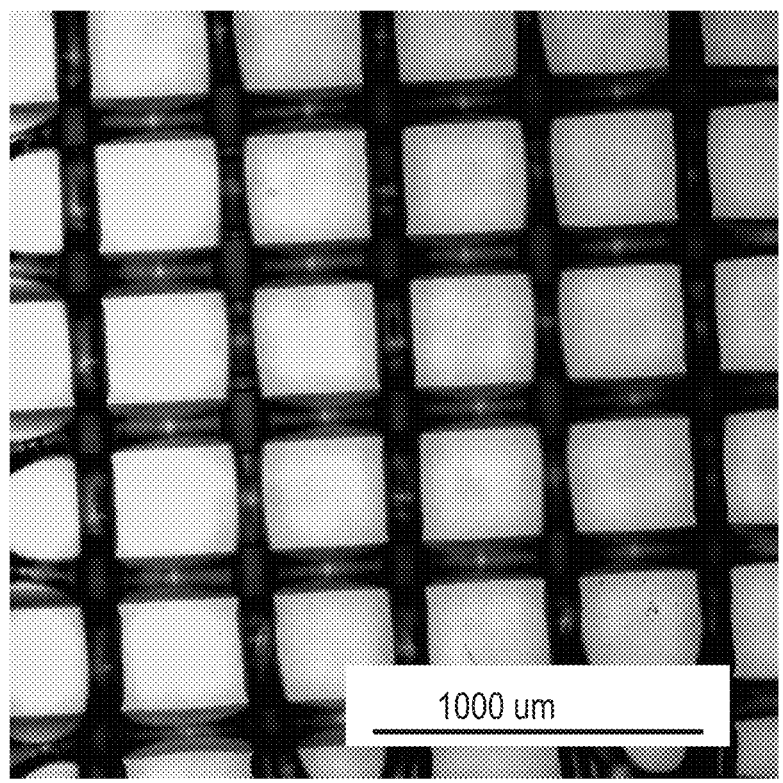
FIG. 18 is a photograph showing the printed hydrogel structure of FIGS. 17A-17B after curing (crosslinking by exposure to 310 nm ultraviolet light), and before soaking with water at 2° C.
Figure 19B:
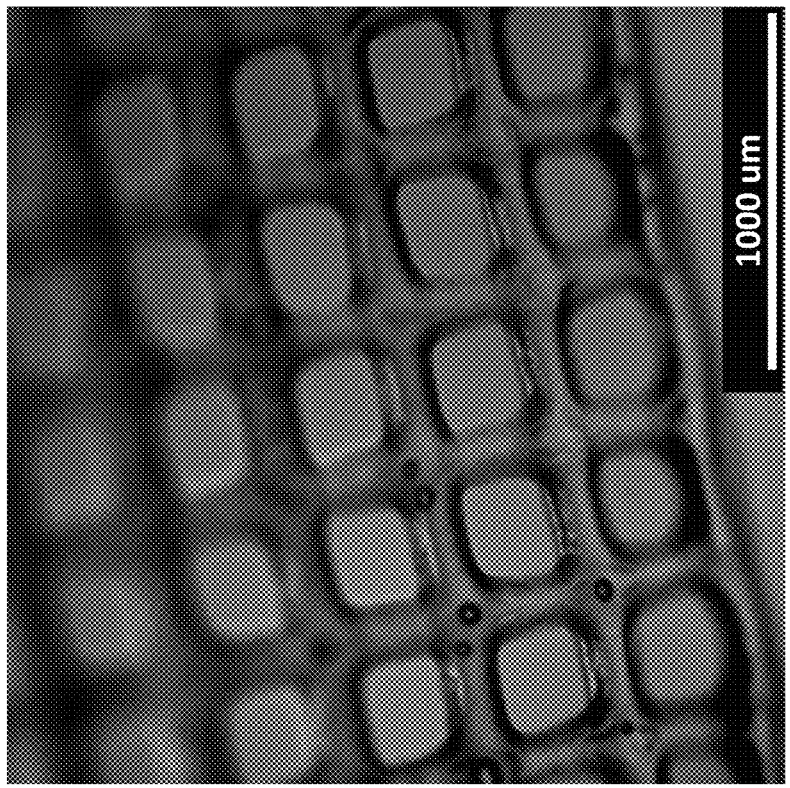
FIGS. 19A-19B are photographic images showing a top-down view and tilted top-down view, respectively, of the crosslinked printed structure of FIG. 18 after soaking in 2° C. water overnight.
Figure 19A:
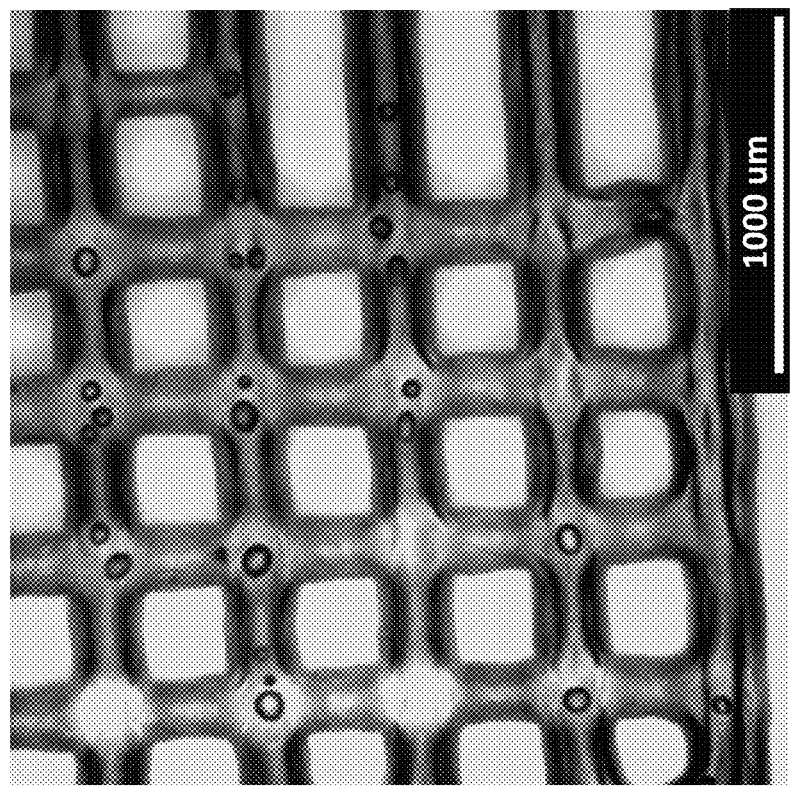
Figure 20:
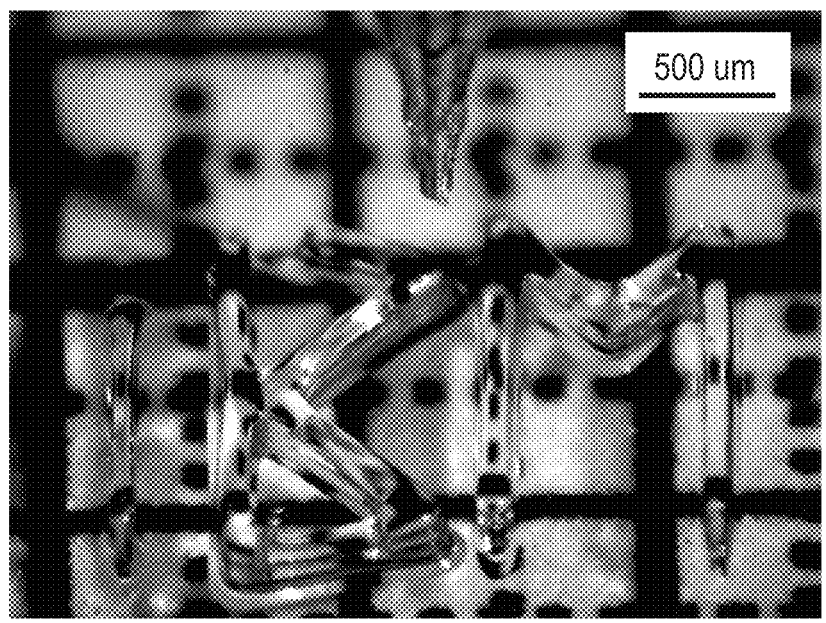
FIG. 20 is a photographic image before curing of the logo "IBM" that was direct write printed using formulation HF-5. Each letter is a stack of hydrogel layers.
Figure 21A:
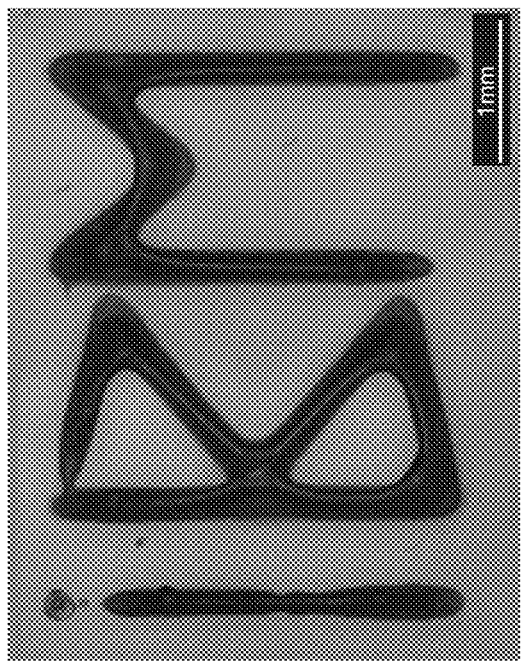
FIGS. 21A-21B are scanning electron micrographs (SEMs) of the structure of FIG. 20 before curing (FIG. 21A) and after curing (FIG. 21B) at 5° C.
Figure 21B:
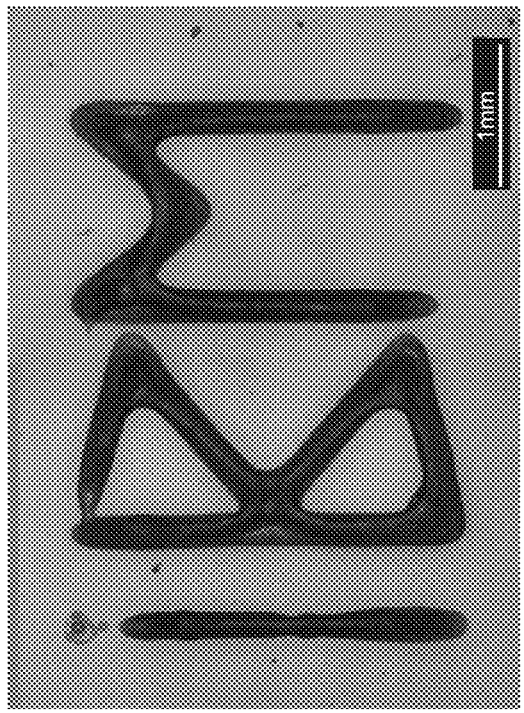

In another direct write printing test, formulation HF-5 was printed using a 100 micrometer diameter conical nozzle operating at 25 psi and a temperature of 24° C. The initial non-crosslinked 3-layered scaffold (FIGS. 17A and 17B, photographic images at two magnifications) shows ordered and self-supporting features. FIG. 18 (photograph) shows the scaffold of FIGS. 17A and 17B after curing (crosslinking), but before soaking with water at 2° C. FIGS. 19A and 19B are photographic images showing two views of the crosslinked scaffold structure after soaking in 2° C. water overnight. FIG. 19A is a top-down view. FIG. 19B is a tilted top-down view. The sample remained in the gel phase, indicating the material is chemically crosslinked. FIG. 20 is a photographic image of another 3D printed structure "IBM" before curing. The letters of the structure show no sagging of the hydrogel bottom layers. FIGS. 21A and 21B are SEMs of the structure of FIG. 20 before curing (FIG. 21A) and after curing (FIG. 21B) at 5° C. No significant distortion of the letters was observed after the curing process.

Direct Write Printing of a Formulation Containing Cells

Example 38 (Comparative)

Preparation of formulation HF-11 containing F-127 and bacterial cells. HF-11 was prepared as follows. F-127 was dissolved in tryptic soy broth (TSB) containing healthy pre-stained *E. coli* bacteria to obtain a 30 wt % polymer gel.

Figure 22A:
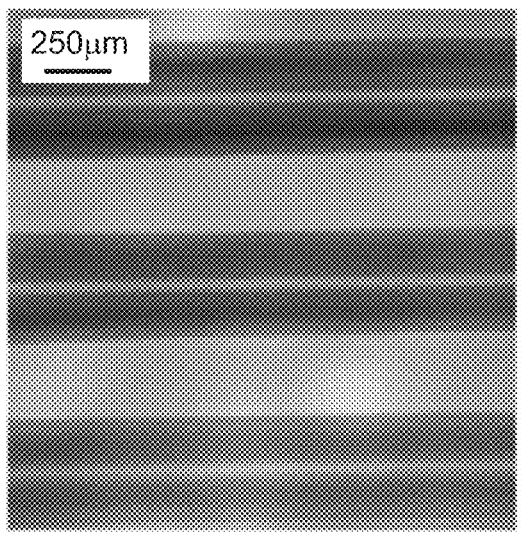
FIG. 22A is a bright field image of a raster line printed using formulation HF-11 containing F-127 and bacterial cells.
Figure 22B:
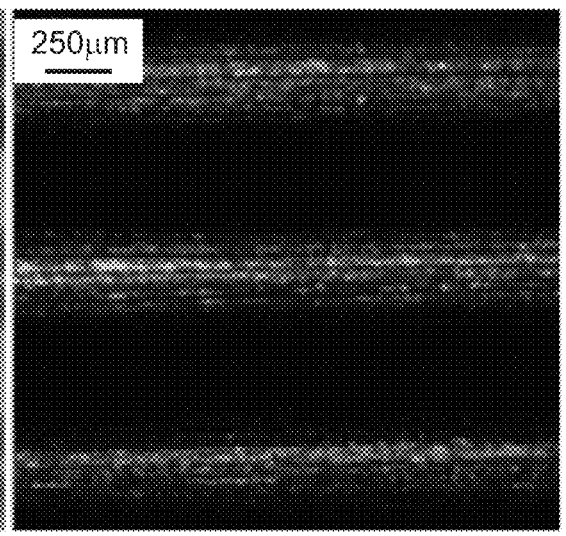
FIG. 22B is a photograph obtained by fluorescent imaging of the raster line printed using formulation HF-11 containing F-127 and bacterial cells. Live bacteria appear as the lighter shade of gray.

A raster line was printed using HF-11, resulting in the structure of FIG. 22A (bright field image). The presence of the healthy bacteria was confirmed by fluorescent imaging (FIG. 22B, photograph, bacteria appear as a lighter shade of gray).

Example 39

Preparation of formulation HF-12 containing TBC-1 and pre-stained bacterial cells. HF-12 was prepared as follows. TBC-1 was dissolved in TSB containing healthy pre-stained E. coli bacteria to obtain a 16 wt % polymer gel.

Figure 23:
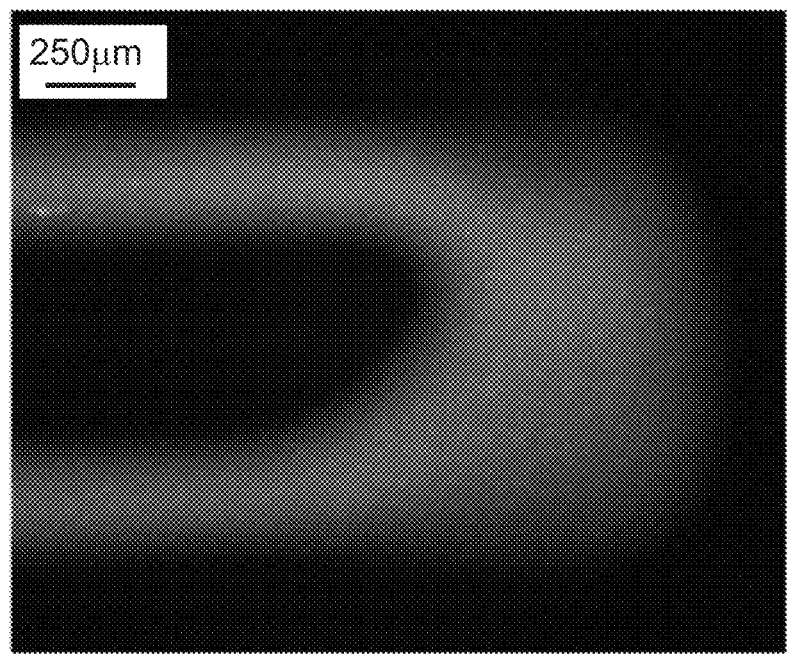
FIG. 23 is a photograph obtained by fluorescent imaging of a circular printed object using formulation HF-12 containing TBC-1 and bacterial cells. Live bacteria appear as the lighter shade of gray.

A circular structure was printed using HF-12. The presence of live bacterial cells in the non-crosslinked gel structure was confirmed by fluorescent imaging (FIG. 23, photograph, bacteria appear as lighter shade of gray).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A crosslinkable composition, comprising:
water;
an ABA type polyether triblock copolymer comprising a central hydrophilic poly(ethylene oxide) block (block B) linked to two peripheral hydrophobic polyether blocks (blocks A), wherein each of the blocks A comprises a random copolymer of i) a first repeat unit of formula (2):

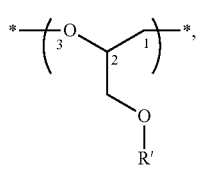

(2)

wherein R' is a monovalent $C_1$-$C_{10}$ hydrocarbon group selected from the group consisting of saturated alkyl groups and aromatic groups, and ii) a second repeat unit of formula (3):

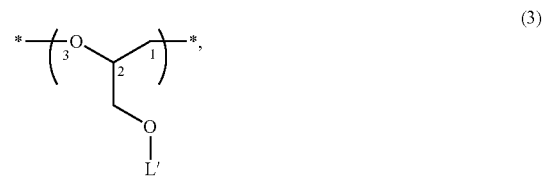

(3)

wherein L' is a monovalent $C_1$-$C_{10}$ hydrocarbon radical comprising an ene group (*—CH=$CH_2$) capable of undergoing a thiol-ene reaction;
a water-soluble crosslinking agent comprising two or more methylenethiol groups (*—$CH_2$SH); and
a photoinitiator capable of abstracting hydrogen from a thiol group when exposed to ultraviolet light of wavelength 10 nm to 400 nm;
wherein
the triblock copolymer, the crosslinking agent, and the photoinitiator are in contact with the solvent,
the composition is a liquid at a temperature between 0° C. and about 10° C. and a shear-thinning viscoelastic solid at a temperature of about 15° C. to about 45° C. before crosslinking.

2. The composition of claim 1, wherein the composition is suitable as an ink for a direct write printing process using an extruding print-head operating at a temperature of about 15° C. to about 45° C.

3. The composition of claim 1, wherein the composition comprises the triblock copolymer in an amount of about 10-30 wt %, based on total weight of the composition.

4. The composition of claim 1, wherein R' is iso-propyl.

5. The composition of claim 4, wherein L' is allyl.

6. The composition of claim 1, wherein the number average molecular weight (Mn) of block B is at least 3 times the Mn of each of blocks A.

7. The composition of claim 1, wherein the molar ratio of first repeat unit:second repeat of the triblock copolymer is about 100:1 to 3:1.

8. The composition of claim 1, wherein each of the blocks A has a number average molecular weight (Mn) of about 2400.

9. The composition of claim 1, wherein the crosslinking agent is selected from the group consisting of 1,2-ethanedithiol, 1,3-propanedithiol, and 1,4-dithiothreitol, and materials of formula (7):

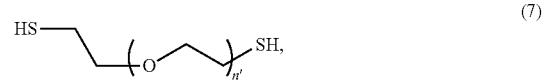

(7)

wherein n' represents average degree of polymerization, and n' has a value of 1 to 300.

10. The composition of claim 1, wherein the crosslinking agent is selected from the group consisting of 1,2-ethanedithiol, 1,4-dithiothreitol, and combinations thereof.

11. The composition of claim 1, wherein the photoinitiator is capable of abstracting hydrogen from a thiol when exposed to ultraviolet light having a wavelength between 300 nm and 400 nm.

12. The composition of claim 1, wherein the photoinitiator is an alpha-hydroxyalkylphenylketone.

13. The composition of claim 1, wherein triblock copolymer comprises the first repeat unit and the second repeat unit in a molar ratio of about 10:1 to 8:1.

14. A film layer comprising the composition of claim 1.

15. A method of printing, comprising:
providing a direct-write printer comprising a printer reservoir containing the composition of claim 1 at a temperature of about 15° C. to about 45° C., the printer equipped with an extruding print-head capable of disposing microdrops and/or strands of the composition pattern-wise onto a surface of a substrate;
extruding the microdrops and/or the strands of the composition from the print-head onto the surface using one or more passes of the print-head over the surface, thereby forming an initial structure comprising a stack of one more patterned layers of the composition disposed on the surface, the layers comprising a self-supporting non-covalently crosslinked hydrogel form of the composition; and
flood-exposing the initial structure with ultraviolet light, thereby forming a photo-cured structure comprising a stack of one more photo-cured patterned layers, the photo-cured patterned layers comprising covalently crosslinked triblock copolymer.

16. The method of claim 15, wherein the ultraviolet light has a wavelength between 300 nm and 400 nm.

17. The method of claim 15, comprising separating the photo-cured structure from the substrate.

18. The method of claim 15, wherein said flood-exposing the initial structure with ultraviolet light initiates a thiol-ene reaction.

19. The method of claim 15, wherein the photo-cured structure is suitable as a scaffold for growing living cells thereon.

20. The photo-cured structure formed by the method of claim 15.

* * * * *